(12) United States Patent
Funamura et al.

(10) Patent No.: US 7,584,767 B2
(45) Date of Patent: Sep. 8, 2009

(54) CONNECTOR

(75) Inventors: Shigeaki Funamura, Fukuroi (JP);
Ichiro Kitani, Fukuroi (JP); Yosuke Sakai, Fukuroi (JP); Katsuki Nagata, Fukuroi (JP); Norifumi Fujiwara, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 276 days.

(21) Appl. No.: 11/690,281

(22) Filed: Mar. 23, 2007

(65) Prior Publication Data

US 2007/0233046 A1 Oct. 4, 2007

Related U.S. Application Data

(63) Continuation-in-part of application No. 11/673,102, filed on Feb. 9, 2007.

(30) Foreign Application Priority Data

Mar. 31, 2006 (JP) ............................. 2006-098646

(51) Int. Cl.
*F16K 11/085* (2006.01)

(52) U.S. Cl. ...................... 137/625.47; 137/625.4; 251/149.1; 604/248

(58) Field of Classification Search ............. 251/149.1, 251/149.6; 137/625.4, 625.41, 625.46, 625.47; 604/248, 256, 905
See application file for complete search history.

(56) References Cited

U.S. PATENT DOCUMENTS

| | | | | | |
|---|---|---|---|---|---|
| 4,207,923 | A | * | 6/1980 | Giurtino | 137/625.47 |
| 5,135,026 | A | * | 8/1992 | Manska | 137/555 |
| 5,144,972 | A | * | 9/1992 | Dryden | 137/15.18 |
| 5,203,775 | A | * | 4/1993 | Frank et al. | 604/256 |
| 5,242,432 | A | * | 9/1993 | DeFrank | 604/284 |
| 5,360,413 | A | * | 11/1994 | Leason et al. | 604/249 |
| 2002/0082586 | A1 | | 6/2002 | Finley et al. | |
| 2003/0105452 | A1 | | 6/2003 | Mayer | |

FOREIGN PATENT DOCUMENTS

| | | |
|---|---|---|
| EP | 0629418 B1 | 1/2005 |
| JP | 56-43311 | 10/1981 |
| JP | 08-206230 | 8/1996 |
| JP | 2003-159336 | 6/2003 |
| WO | WO 2005107847 A1 | 11/2005 |

* cited by examiner

*Primary Examiner*—John K Fristoe, Jr.

(57) ABSTRACT

A connector has a connection port closed by a sealing member. The connection port is attached to a first body portion which in turn is connected to a second body portion by an elastic bellows. When a Luer connector is withdrawn from the port, the bellows first extends and then retracts creating an overpressure within the connector.

20 Claims, 39 Drawing Sheets

CONNECTOR

CROSS-REFERENCE TO RELATED APPLICATIONS

This patent application claims the benefit of Japanese Patent Application No. 2006-098646 filed Mar. 31, 2006 and is a continuation-in-part of U.S. application Ser. No. 11/673,102 filed Feb. 9, 2007, the entire contents of which are incorporated herein by reference.

FIELD OF THE INVENTION

The present invention relates to a connector connected to a tube body in which a channel is formed, and in particular, relates to the connector of a closed system that is normally closed and that is opened as necessary to supply liquid to the channel.

BACKGROUND OF THE INVENTION

In medical settings, liquids are often transferred, e.g., transfusions, blood transfusions, artificial dialysis, drawing blood, or the like. For transferring various liquids, a pipe-shaped tube can be used with connectors connected to the tube, and a plurality of liquids can be caused to converge or be shut off. Such connectors, in addition to being used as a coinjection tool attached in the middle of the tube to coinject another liquid medicine into the tube, are used for various applications. For example, in addition to using connectors provided with a switching valve function, they can be used as a three-way stopcock, and objected from support arms normally closed connectors that are attached to the end of a liquid medicine tube so that the supply of liquid from the liquid medicine tube is normally stopped and liquid is supplied as necessary.

Connectors are generally provided with a housing in which a channel space is formed, through which a liquid, such as liquid medicine, flows to the inside. A connection opening connected to the channel is furnished, the channel being connected to the channel space through the connection opening through which liquid medicine flows. An opening for supply of a liquid from the outside is also formed in the housing. The Luer part of a syringe is inserted into the opening and liquid medicine or the like is introduced into the channel space through the opening.

However, with an open connector not connected at the opening, that is, without a Luer part being inserted, the outside and the channel space are always connected, and liquid medicine in the channel part sometimes overflows to the outside. There is also the risk of bacteria growing in areas where liquid medicine adheres near the opening. For this reason, in recent years, closed connectors have often been used such that when a normally closed valve member is attached to the opening and no Luer part is inserted, the opening is blocked in leakproof fashion.

With closed connectors such as this, a slit is generally formed in the valve member attached to the opening, for example see Japanese Kokai Patent Application No. 2003-159336 or Japanese Kokai Patent Application No. Hei 8[1996]-206230. Then, in the normal state (Luer part not inserted, no liquid supplied), this slit is closed. On the other hand, to supply a liquid, a Luer part is inserted into the slit. Then the slit opens and the Luer part is exposed to the channel space in the housing. By injecting the liquid to be supplied from a syringe at this stage, liquid is discharged from the Luer part into the channel space and supplying of the liquid is accomplished. When supplying of liquid is completed, the Luer part is pulled from the slit. Then the slit closes again and the opening is closed.

SUMMARY OF THE INVENTION

In one aspect, a connector includes a housing having a plurality of connection ports. The housing defines a fluid flow through channel. The connection ports are selectably connectable via the through channel. One of the connection ports is an injection port that incorporates a valve member for sealingly closing the injection port. The valve member is arranged so as to be movable in a direction towards the through channel in response to an applied external pressure so as to open the injection port to fluid flow. The housing includes a first body part and a second body part. The second body part incorporates the injection port. The first body part is connected to the second body part by an elastic member.

In another aspect, a connector includes a housing. The housing has an opening portion opened to the outside and a connecting port connected to a tube. The connecting port has a flow channel space that allows for the flow of liquid through the connecting port formed inside it. The connector includes a closure comprising a valve member for attachment to the opening portion and allows a liquid from outside to flow into the flow channel space after the valve member is opened. The valve member has a main body portion that seals the opening portion liquid tight and can be moved to the side of the flow channel space under pressing force from the outside. The valve member includes a supporting portion that is connected to the main body portion and is engaged to the housing. The supporting portion has an elastic force that acts on the main body portion when the main body portion moves to the side of the flow channel space under pressing force from the outside. The main body portion has an outer surface facing the outside and an inner surface facing the flow channel space while the opening portion is blocked liquid tight. A connecting surface is formed on the outer surface and is connected to the flow channel space when the main body portion is pressed into the side of the flow channel space under pressing force from outside. The housing comprises a first body part and a second body part. The second body part incorporates the opening portion. The first body part is connected to the second body part by an elastic member.

In another aspect, a connector has a housing. The housing has an opening portion opened to the outside and a connecting port connected to a tube. The connecting port includes a flow channel space that allows for the flow of liquid through the connecting port formed inside it. The connector comprises a valve member for attachment to the opening portion and allows a liquid from outside to flow into the flow channel space after opening of the valve member. The valve member includes a main body portion that seals the opening portion liquid tight and can be moved to the side of the flow channel space under the pressing force from the outside. The valve member includes a supporting portion that is connected to the main body portion and is engaged to the housing. The supporting portion has an elastic force that acts on the main body portion when the main body portion moves to the side of the flow channel space under pressing force from the outside. The main body portion has an outer surface facing the outside and an inner surface facing the flow channel space while the opening portion is blocked liquid tight. A connecting surface is formed on the outer surface and is connected to the flow channel space when the main body portion is pressed into the side of the flow channel space under pressing force from outside. The housing comprises a first body part and a second body part. The second body part incorporates the opening portion. The first body part is connected to the second body part by an elastic member.

In yet another aspect, a fluid through-flow connector has at least one connection port. The connection port comprises a connection port housing. The housing has an inner surface and an outer surface. The inner surface defines an inner volume. The connector further comprises a sealing member. The sealing member has an inner portion that extends within the inner volume and at least one outer portion that extends externally of the housing. The inner portion includes an inner slit that extends from a lower surface of the inner portion. The sealing member is of an elastically deformable material. The sealing member is arranged such that it is deformable from a first closed state in which the sealing member is arranged in a fluid sealing configuration to a second open state in which the sealing member is arranged in a fluid non-sealing configuration and in which the inner portion is displaced into the inner volume and in which the at least one outer portion exerts a restoring force on the inner portion urging the inner portion to return to the first closed state. The deformation from the first closed state to the second open state is caused by the making of a connection to the connection port. The housing comprises a first body part and a second body part. The second body part incorporates the connection port. The first body part is connected to the second body part by an elastic member.

Other features will be in part apparent and in part pointed out hereinafter. Various refinements exist of the features noted in relation to the above-mentioned aspects of the present invention. Further features may also be incorporated in the above-mentioned aspects of the present invention as well. These refinements and additional features may exist individually or in any combination. For instance, various features discussed below in relation to any of the illustrated embodiments of the present invention may be incorporated into any of the above-described aspects of the present invention, alone or in any combination.

DETAILED DESCRIPTION OF THE DRAWINGS

First Embodiment

Figure 1:
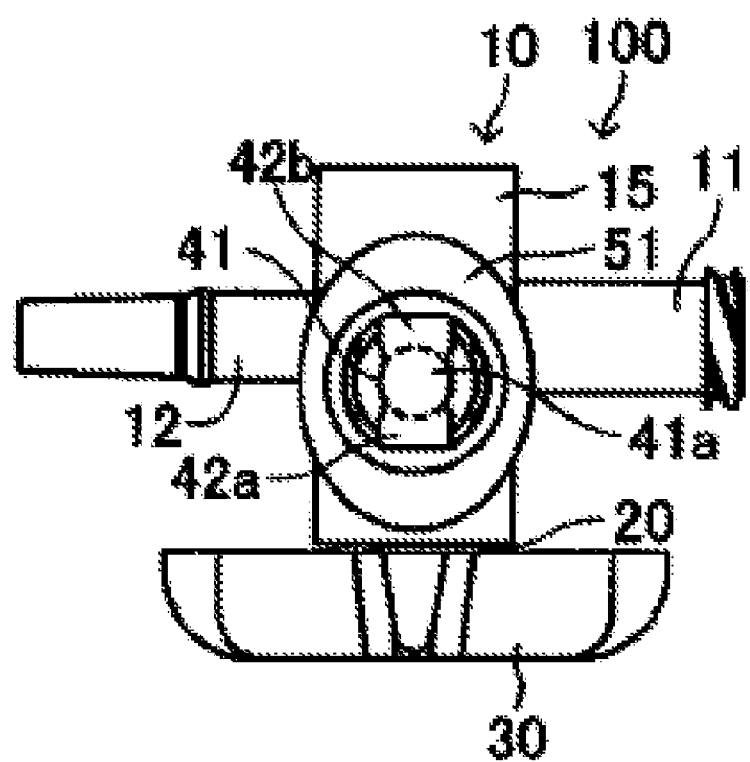
FIG. 1 is a plan view of a three-way stopcock pertaining to a first embodiment of the present invention.
Figure 2:
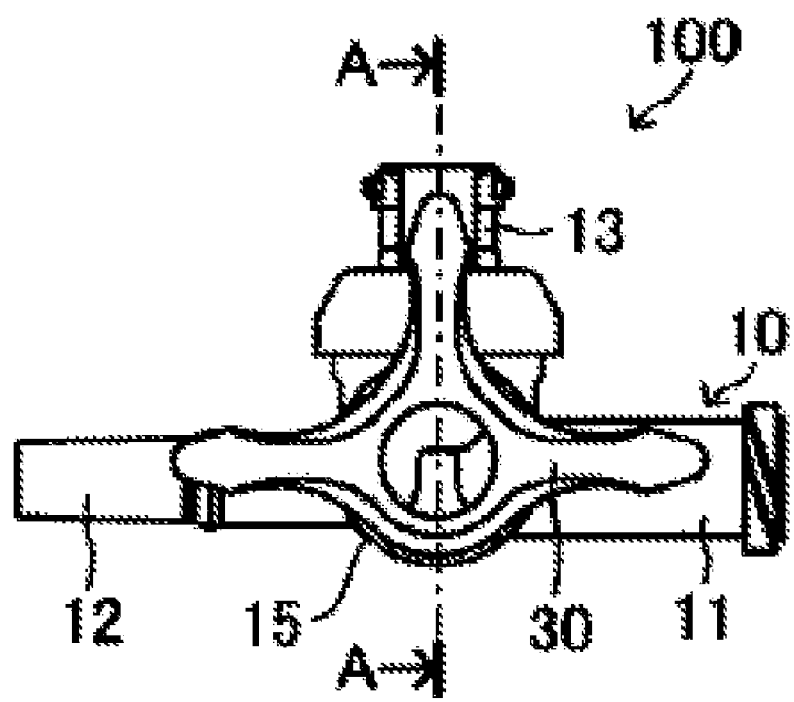
FIG. 2 is a front view of a three-way stopcock pertaining to the first embodiment of the present invention.
Figure 3:
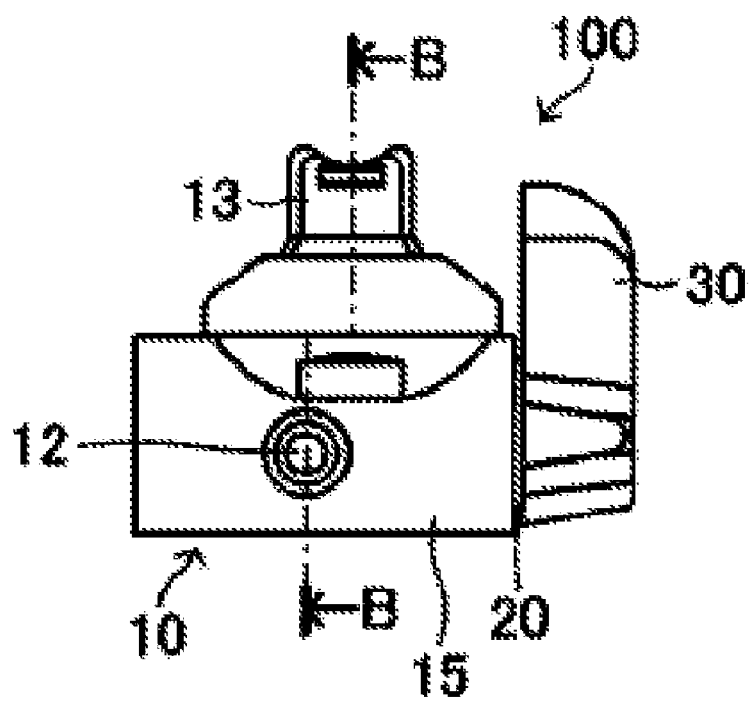
FIG. 3 is a left side view of a three-way stopcock pertaining to the first embodiment of the present invention.

Below, a connector pertaining to the present invention is explained in detail using figures. First, an example wherein a connector is used as a three-way stopcock is explained as the first embodiment. FIG. 1 is a plan view of a three-way stopcock pertaining to the first embodiment of the present invention, FIG. 2 is a front view, and FIG. 3 is a left side view relative to FIG. 2 as the front view. As can be seen from these figures, three-way stopcock (100) is constituted with a housing (10), a plug body (20) and a grip part (30). Plug body (20) and grip part (30) are formed integrally, and plug body (20) is installed in housing (10).

Housing (10) is provided with a tubular part (15), and a first branch tube (11), second branch tube (12) and third branch tube (13), which are 3 branch tubes attached to tubular part (15). Branch channels (first branch channel (11*a*), second branch channel (12*a*) and third branch channel (13*a*)) are respectively formed in the branch tubes, and each branch channel is open to the inner wall of tubular part (15). Note that in this embodiment, polycarbonate (PC) is used as the material for housing (10), but in addition, polypropylene (PP), polyethylene terephthalate (PET) or another resin material can be preferentially used.

Figure 4:
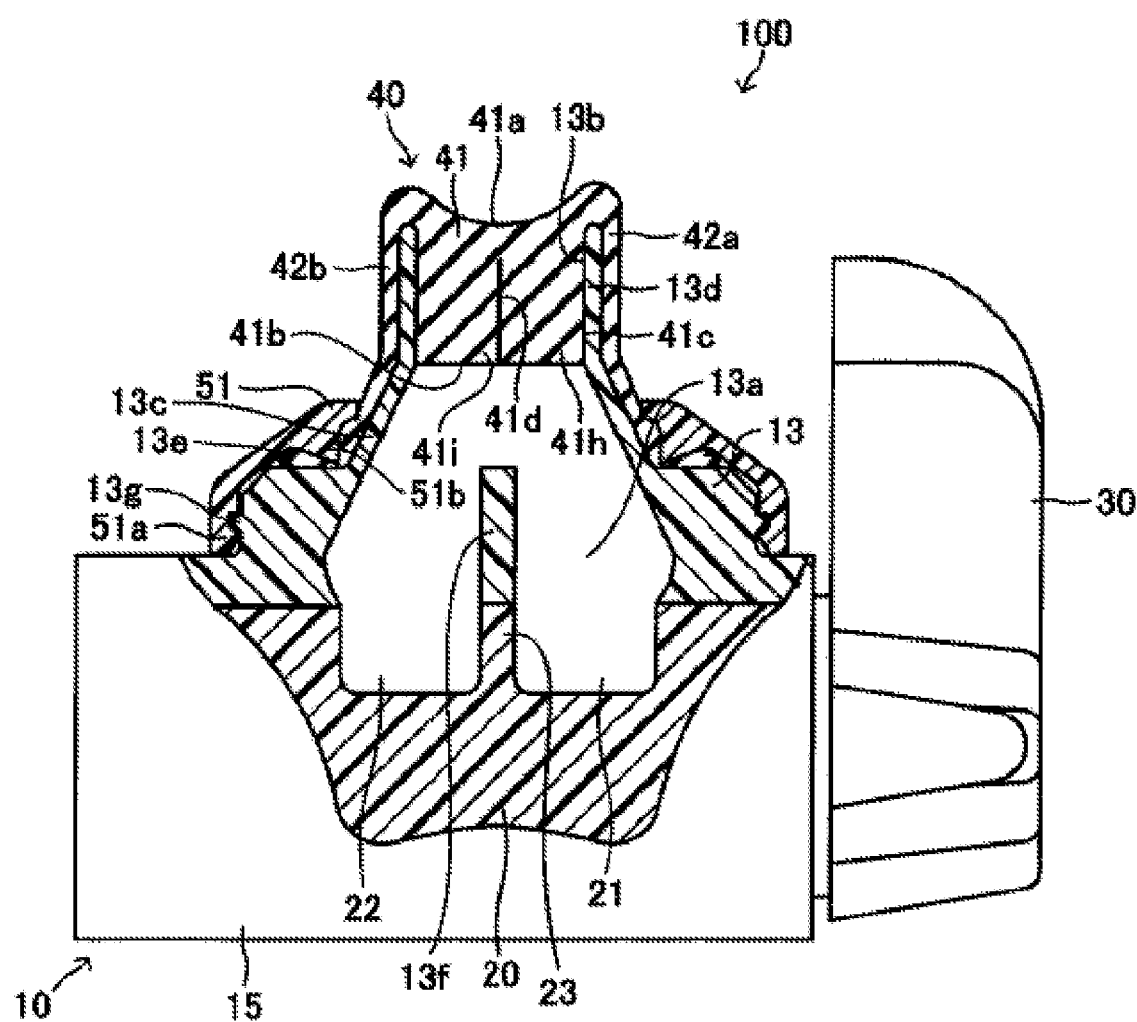
FIG. 4 is a partial cross section at A-A in FIG. 2.
Figure 5:
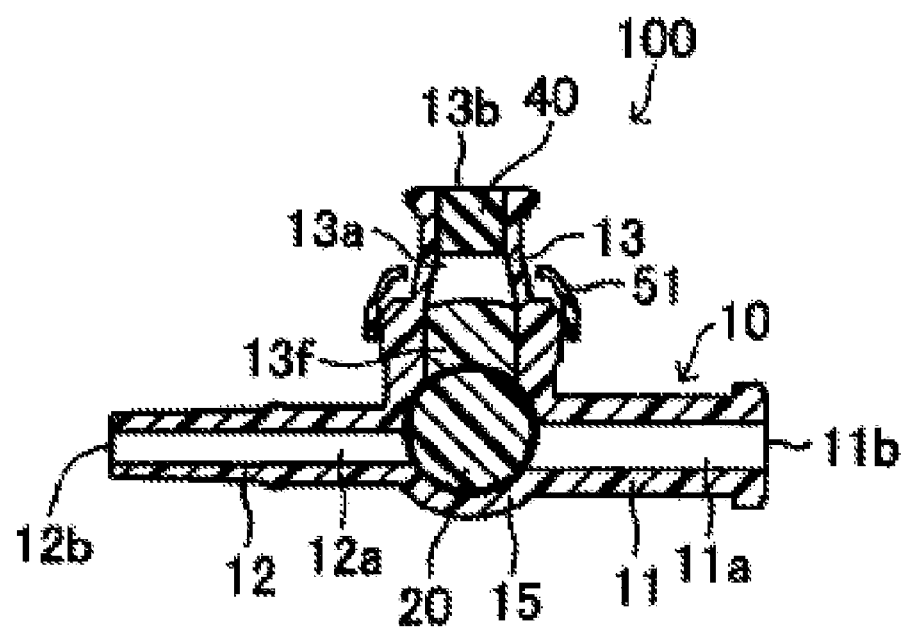
FIG. 5 is cross section B-B in FIG. 3.

FIG. 4 is a partial cross section of A-A in FIG. 2, and FIG. 5 is cross section B-B in FIG. 3. As shown in FIG. 5, plug body (20) is rotatably fitted in the inner circumference of tubular part (15) of housing (10). As shown in FIG. 4, two grooves (21) and (22) are formed in the outer circumference of plug body (20). Grip part (30) is attached to one end of plug body (20). Grip part (30) is provided with three arm parts and is turned integrally with plug body (20). Therefore, plug body (20) also rotates in the inner circumference of tubular part (15) when grip part (30) is rotated. The arrangement of grooves (21) and (22) formed in the outer circumference of plug body (20) changes with rotation of plug body (20). Connecting or closing off of the branch channels formed in the branch tubes can be selected by changing the arrangement of grooves (21) and (22) in various ways.

In this embodiment, plug body (20) and grip part (30) are formed integrally. Polyethylene (PE) is used as material, but in addition, polyoxymethylene (POM), polypropylene (PP) or another resin can be used.

As can be seen from FIG. 5, first branch tube (11) is connected to the right side of tubular part (15) in the figure and opening (11b) of first branch channel (11a) opens to the right in the figure. Second branch tube (12) is connected to the left side of tubular part (15) in the figure, and opening (12b) of second branch channel (12a) opens to the left in the figure. Additionally, third branch tube (13) is connected to the top of tubular part (15) in the figure, and opening (13b) of third branch channel (13a) opens to the top in the figure. Note that in this embodiment, the space in third branch channel (13a) and the channel space connected to it correspond to the channel space in embodiments of the present invention, and first branch tube (11) and second branch tube (12) correspond to the connection openings in embodiments of the present invention.

First branch tube (11), second branch tube (12) and third branch tube (13) are connected to tubular part (15) at intervals of approximately 90 degrees. First branch tube (11) and second branch tube (12) are arranged facing on either side of tubular part (15). Third branch tube (13) is disposed at a position separated by 90 degrees around the circumference of tubular part (15) from both first and second branch tubes (11) and (12), and third branch channel (13a) is formed perpendicular to first branch channel (11a) and second branch channel (12a).

As shown in FIG. 4, third branch tube (13) is formed extending in a vertical direction from the side periphery of tubular part (15), and is constituted with a tapered part (13c), which has a tapered inner wall whose inner diameter becomes smaller farther from tubular part (15), and a cylindrical part (13d) extending upward in the figure from the tip (small diameter end) of tapered part (13c). Tapered part (13c) forms third branch channel (13a) with its inner circumferential surface, and a step part (13e) is formed in its outside surface. The channel space in third branch channel (13a) formed inside tapered part (13c) can connect with the abovementioned grooves (21) and (22), and liquid in grooves (21) and (22) can flow through third branch channel (13a).

A partition (13f) as shown in the figure is furnished in third branch channel (13a). Partition (13f) is formed in a position where its axial orientation coincides with partition (23) formed between the two grooves (21) and (22) formed in the outer circumference of plug body (20). As shown in FIG. 4, it is formed between grooves (21) and (22). It is therefore, intended that liquids in the two grooves (21) and (22) will not pass over partition (13f) and cannot flow directly into each other.

Opening (13b) of third branch channel (13a) is located at the top of cylindrical part (13d) of third branch tube (13) in the figure. A valve member (40) is attached to opening (13b). Valve member (40) is constituted with a main body (41), a first support arm (42a) and a second support arm (42b), and these are formed integrally of a rubber-like material. Main body (41) is inserted into opening (13b), blocking opening (13b) in leakproof fashion. Main body (41) is formed in a round columnar shape, and its outline is formed by outside surface (41a) on the side facing the outside, inside surface (41b) at the end facing the channel space in third branch channel (13a), and side circumferential surface (41c) that is the circumferential surface between outside surface (41a) and inside surface (41b), as shown in the figure. Note that opening (13b) of third branch channel (13a) corresponds to the opening in embodiments of the present invention.

The side circumferential surface (41c) of main body (41) contacts the inner wall of cylindrical part (13d) of third branch tube (13), and it fits elastically in opening (13b). It is thus mounted in opening (13b) so that it can be pushed in toward third branch channel (13a) by pressing outside surface (41a) from the outside.

As shown in the figure, an inner slit (41d) is formed in main body (41). Inner slit (41d) is made by a cut being formed in inside surface (41b), and it is formed extending nearly plumb from the open part toward outside surface (41a). However, inner slit (41d) does not reach outside surface (41a) and is not formed to pass through from inside surface (41b) to outside surface (41a).

Figure 6:
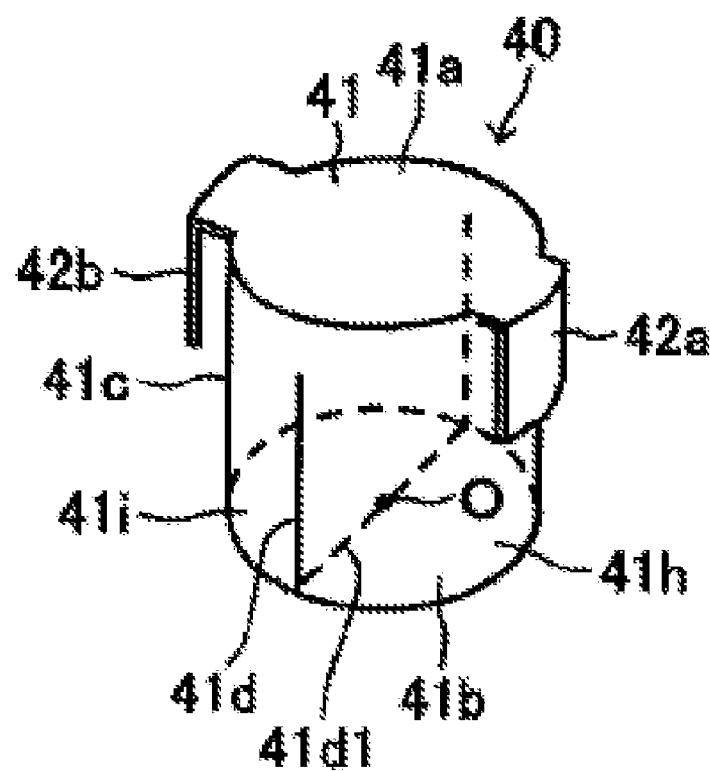
FIG. 6 is an oblique view schematically representing the valve member pertaining to the first embodiment of the present invention.

FIG. 6 is an oblique view that schematically represents valve member (40) in this embodiment. As shown in FIG. 6, opening (41d1) in inside surface (41b) of inner slit (41d) is formed as a straight-line opening (cut) reaching from the edge of the outer periphery of inside surface (41b) through center (0) to the edge on the opposite side. Thus, inside surface (41b) is divided into two parts by inner slit (41d), and main body (41) is also divided into a first portion (41h) and a second portion (41i) by inner slit (41d). However, first portion (41h) and second portion (41i) are not completely separate and are united in the portion at the top of main body (41) shown.

As shown in FIG. 1 [sic], first support arm (42a) and second support arm (42b) are formed extending outward, in the radial direction, from the outer edge of outside surface (41a) of main body (41). In this embodiment, the support arms are each attached at opposite positions of outside surface (41a). As shown in FIG. 4, first support arm (42a) and second support arm (42b) are attached in circumferential positions such that they have approximately plane symmetry when the plane in which inner slit (41d) is formed serves as the plane of symmetry. Support arms (42a) and (42b) pass over the top end of cylindrical part (13d) of third branch tube (13) and run along the outside walls of cylindrical part (13d) and tapered part (13c).

As shown in FIG. 4, a cover (51) made of plastic is attached to the outer periphery of tapered part (13c) of third branch tube (13). Cover (51) is dome-shaped. The center of cover (51) is a circular opening, and the cover is mounted on third branch tube (13) by inserting cylindrical part (13d) of third branch tube (13d) through this opening. It is also attached to third branch tube (13) to cover the entire circumference of tapered part (13c). An annular groove (51a) is formed in the inner circumference at the lower end of cover (51), as shown. Cover (51) is fixed to tapered part (13c) by groove (51a)

engaging with an annular projection (13g) formed on the outer circumference at the lower part of tapered part (13c).

A projection (51b) is also formed at the top of the inner circumference of cover (51), as shown in FIG. 4. Projection (51b) engages in step part (13e) formed in the outer circumference of tapered part (13c). First support arm (42a) and second support arm (42b) are held where projection (51b) engages in step part (13e). Therefore, support arms (42a) and (42b) are held fixed by cover (51) and tapered part (13c). By using support arms (42a) and (42b) that are fixed in this way, main body (41) is supported such that it is suspended by first support arm (42a) and second support arm (42b).

In the three-way stopcock (100) of this embodiment that is constituted as described above, grip part (30) is rotated, groove (21) connects first branch channel (11a) and third branch channel (13a), and groove (22) is connected to second branch channel (12a) and third branch channel (13a). A liquid medicine tube is also attached to first branch tube (11) and second branch tube (12). Liquid medicine is then supplied from the liquid medicine tube connected to first branch tube (11). The liquid medicine then flows into groove (21) of plug body (20) from first branch channel (11a). The liquid medicine in groove (21) passes over partition (21c) and enters third branch channel (13a). The liquid medicine further passes over partition (13f) in third branch channel (13a) and enters groove (22). It then flows into second branch channel (12a) from groove (22). The main channel flow is created in this way.

Here, as shown in FIG. 4, opening (13b) of third branch tube (13) is blocked in leakproof fashion by main body (41) of valve member (40) and is closed. Therefore, the main channel flow circulating as described above does not leak out of third branch tube (13). Also, no impurities from the outside will get into third branch channel (13a) through opening (13b) of third branch tube (13).

Figure 7A:
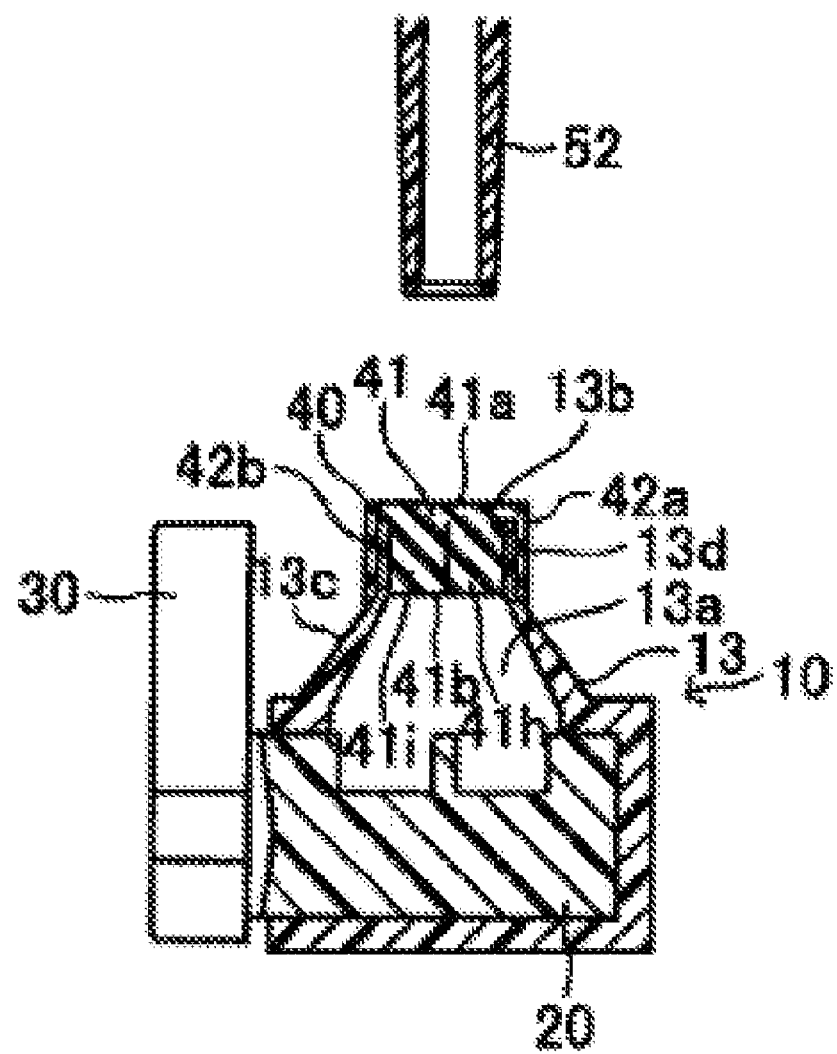
FIG. 7 shows the operation when coinjecting from the third branch tube of the three-way stopcock in the first embodiment of the present invention; (a) shows the situation before the Luer part is inserted into the valve member, (b) when the Luer part is inserted in the valve member but the valve member is still closed, and (c) when the Luer part is inserted into the valve member and the valve member is open.
Figure 7B:
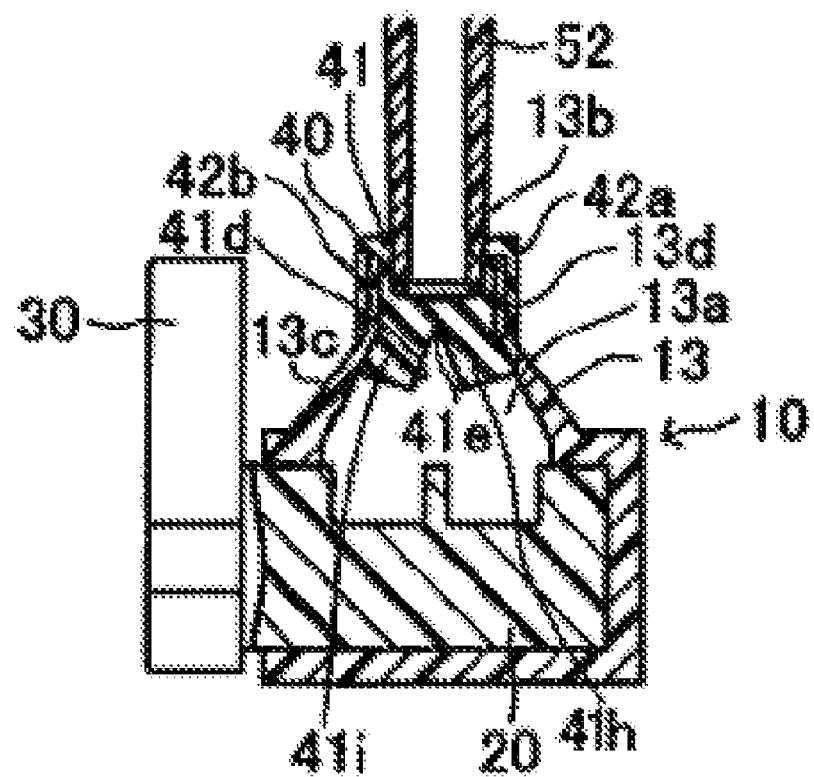
Figure 7C:
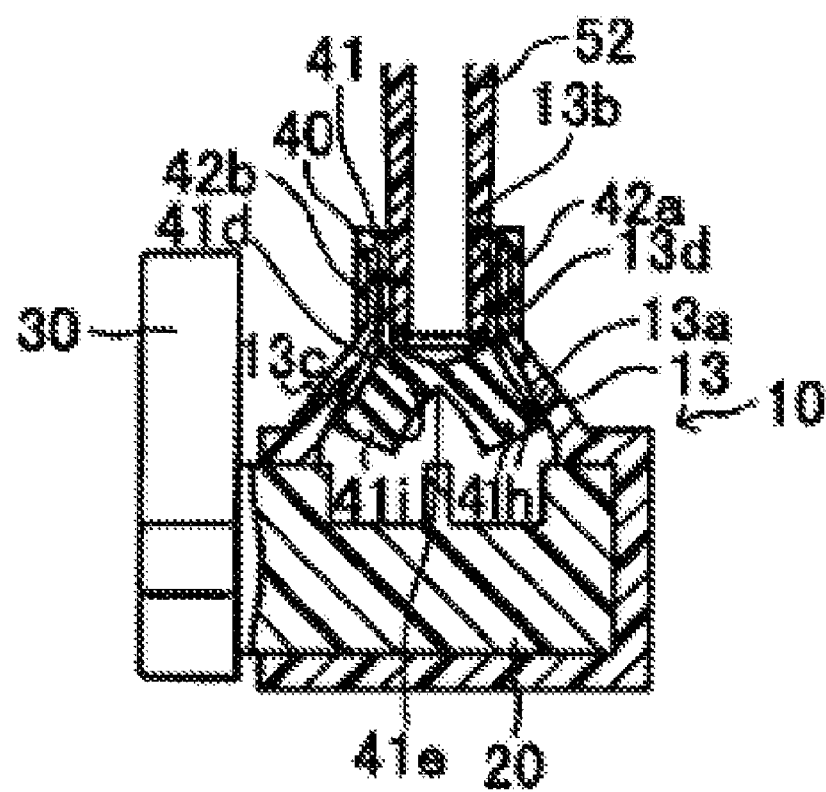
Figure 8A:
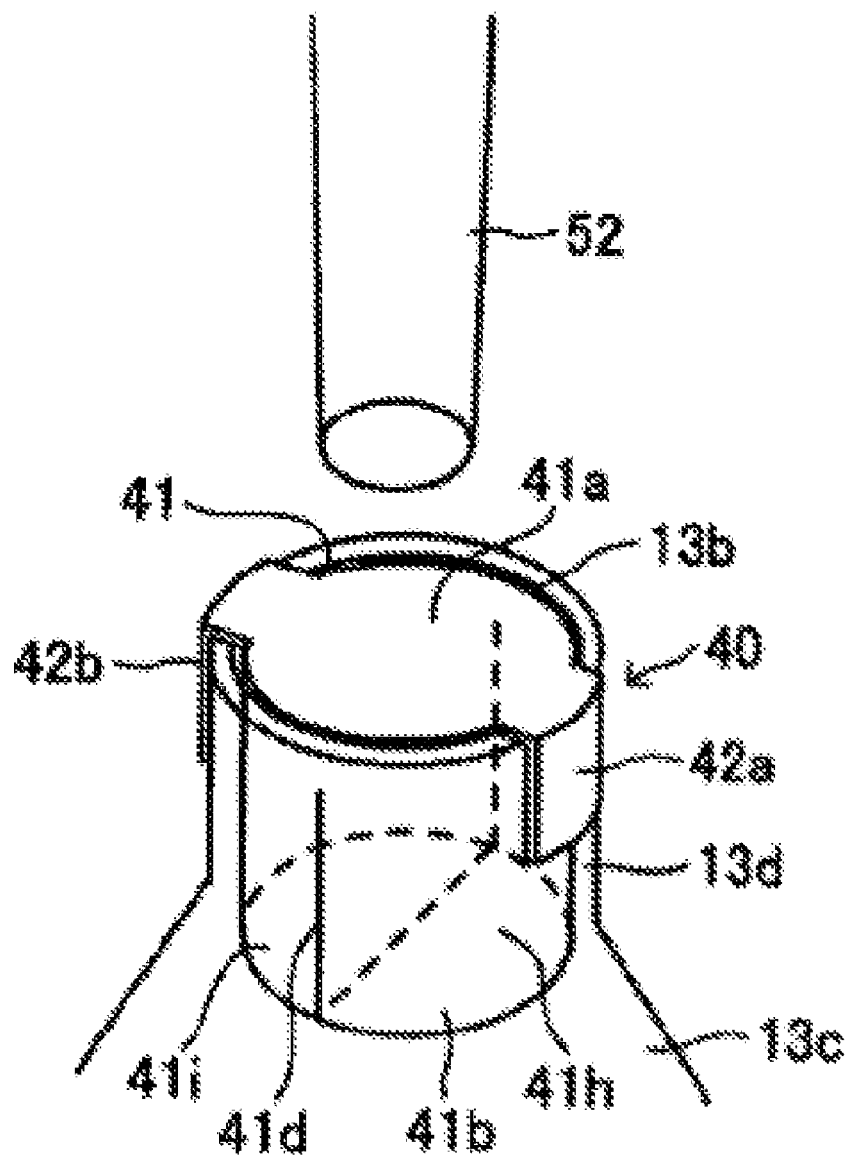
FIG. 8 shows the same operation as FIG. 7 obliquely.
Figure 8B:
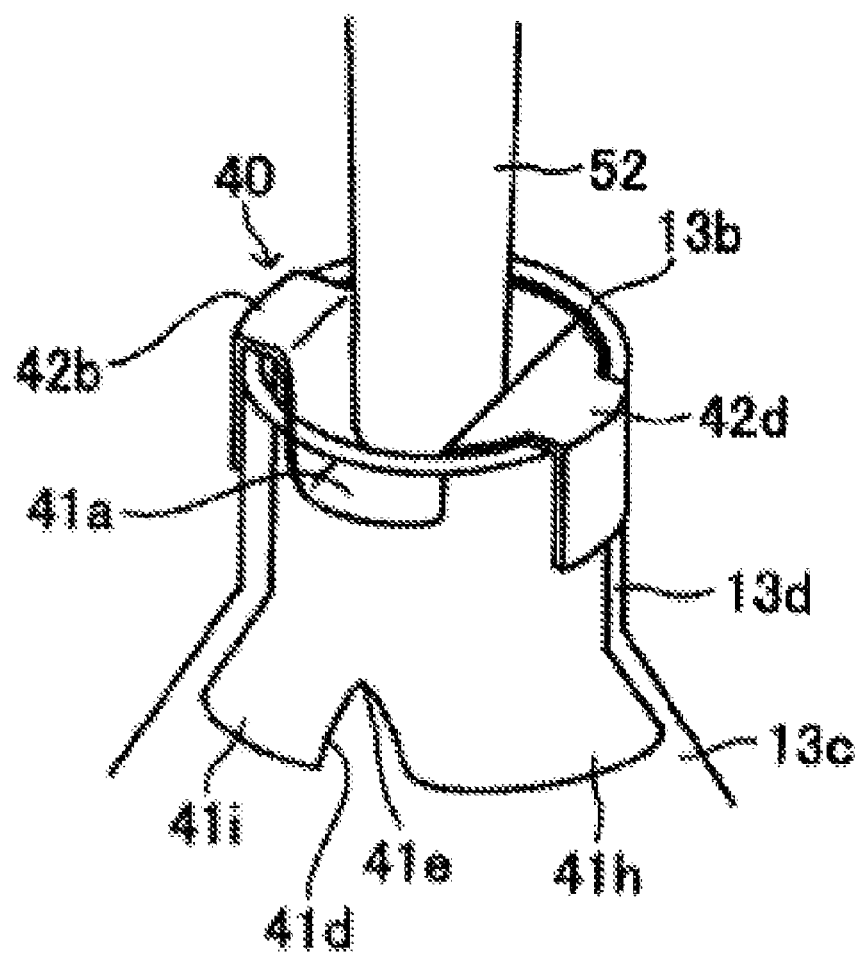
Figure 8C:
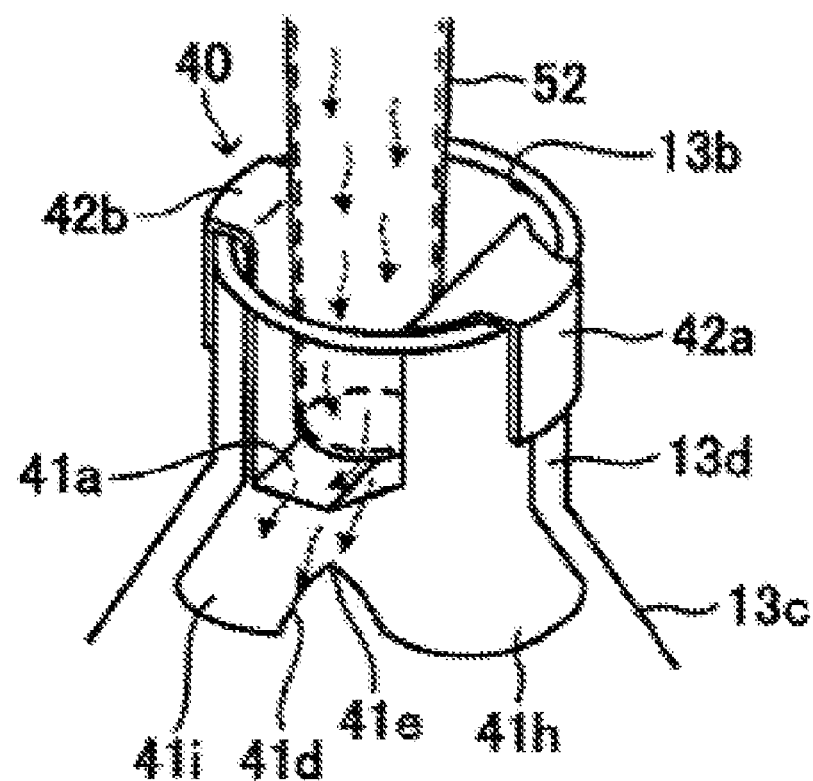

When liquid medicine is coinjected into the main channel from third branch tube (13), the Luer part of a syringe is inserted into main body (41) of valve member (40), opening the valve member. FIGS. 7 (a)-(c) are figures schematically representing the operation up until the Luer part (52) of a syringe is attached to valve member (40) installed in opening (13b) of third branch tube (13) and liquid medicine is supplied to the main channel from the syringe, while FIGS. 8 (a)-(c) show the states in FIGS. 7 (a)-(c) obliquely. FIGS. 7 (a) and 8 (a) show the situation before Luer part (52) is inserted into valve member (40), FIGS. 7 (b) and 8 (b) show valve member (40) still closed, and FIGS. 7 (c) and 8 (c) show Luer part (52) inserted into valve member (40) and valve member (40) opened.

First, as shown in FIGS. 7 (a) and 8 (a), the tip of the Luer part (52) of a syringe filled with liquid medicine to be coinjected is brought close to valve member (40) installed in opening (13b) of third branch tube (13). Then, as shown in FIGS. 7 (b) and 8 (b), the tip of Luer part (52) is pressed against outside surface (41a) of main body (41) of valve member (40) and outside surface (41a) is pushed in toward third branch channel (13a), which is at the bottom in the figure. Then main body (41) is pushed in downward in the figure and first support arm (42a) and second support arm (42b) are stretched by the pushing force of Luer part (52).

Figure 9:
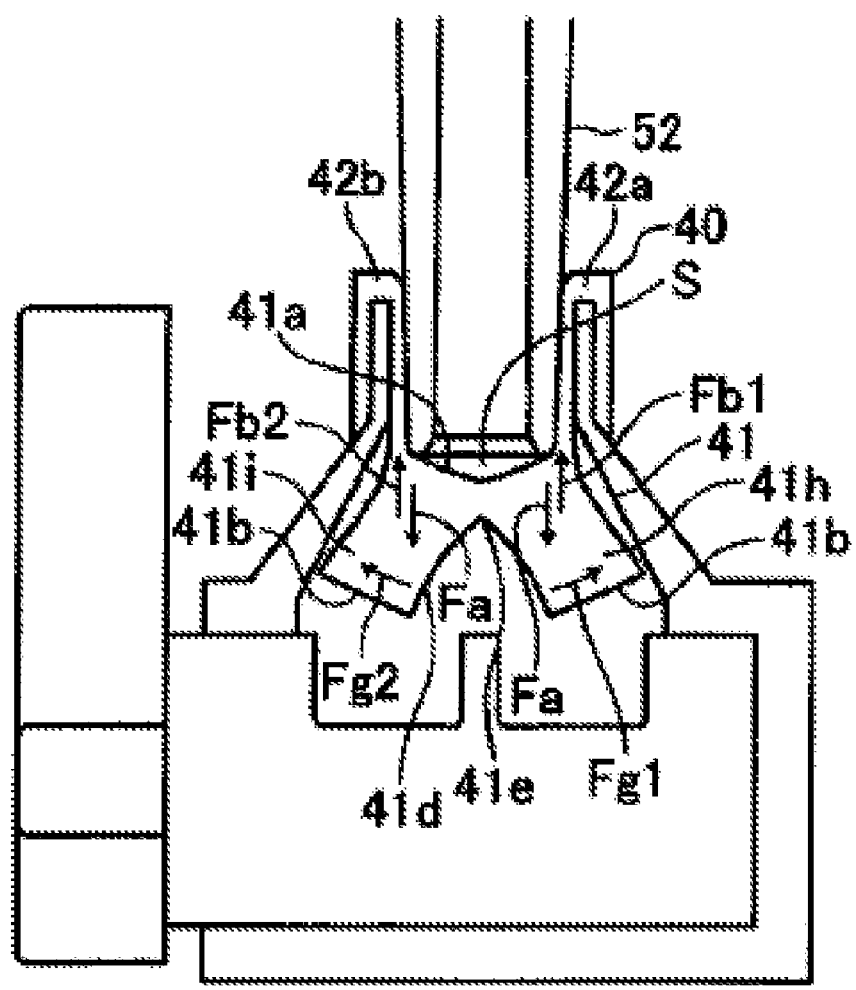
FIG. 9 pertains to the first embodiment of the present invention and shows the relationship between the pushing force and the lifting force acting on the main body of the valve member.

When first and second support arms (42a) and (42b) are stretched, the elastic restoring force from support arms (42a) and (42b) acts on main body (41), and because support arms (42a) and (42b) try to return main body (41) to its original position, a force is generated that attempts to raise main body (41) (lifting force). FIG. 9 shows the relationship between the pushing force from Luer part (52) and the lifting force from first and second support arms (42a) and (42b). As shown in FIG. 9, pushing force (Fa) applied by the open part at the tip of Luer part (52) to main body (41) of valve member (40) acts in a direction (downward in the figure) to push main body (41) toward third branch channel (13a). In contrast to this, lifting force (Fb1) that first support arm (42a) applies to main body (41) acts in a direction to raise main body (41) from third branch channel (13a) to the outside (upward in the figure). In the same way, lifting force (Fb2) that second support arm (42b) applies to main body (41) also acts in a direction to raise main body (41) from third branch channel (13a) to the outside (upward in the figure). Pushing force (Fa) and lifting forces (Fb1) and (Fb2) act in opposite directions from different positions, so that a force couple acts on main body (41).

The force couple acts between pushing force (Fa) and lifting force (Fb1), and between pushing force (Fa) and lifting force (Fb2). The lines of action of lifting forces (Fb1) and (Fb2) are positioned radially toward the outside of main body (41), relative to the lines of action of pushing force (Fa). Therefore, the center of main body (41) is pushed in toward third branch channel (13a), and the outer circumference is pulled up by support arms (42a) and (42b). In this state, main body (41) is subjected to a force causing it to fold inward at the outside surface (41a) side, while at the inside surface (41b) side of main body (41) is subjected to a force pulling it from the center toward the outer circumference as indicated by arrows (Fg1) and (Fg2) in the figure.

Inner slit (41d) is also formed in main body (41), and inner slit (41d) is formed to divide inside surface (41b) into two parts. The plane in which inner slit (41d) is formed also serves as the plane of symmetry between the portion where first support arm (42a) is attached to main body (41) and the portion where second support arm (42b) is attached to main body (41), and of first portion (41h) and second portion (41i) divided by inner slit (41d), first portion (41h) is supported by the first support arm (41a) and second portion (41i) is supported by the second support arm (42b). Therefore, the force indicated by arrow (Fg1) acts primarily on first portion (41h), and the force indicated by arrow (Fg2) acts primarily on second portion (41i). The result, as shown in FIGS. 7 (c), 8 (c) and 9, is that inner slit (41d) opens, and first portion (41h) and second portion (41i) divided by inner slit (41d) separate in the region at the bottom in the figures.

As can be seen from FIG. 9, when inner slit (41d) opens as described above, base portion (41e) of inner slit (41d) is pushed downward in the figure. Then, pulled along by this, outside surface (41a) of main body (41) is also forced down in the figure, and a depression (S) is formed near the center. Depression (S) is formed as a groove running from the outer circumferential edge of outside surface (41a) to the edge on the opposite side along inner slit (41d). Depression (S) is also formed between the open part at the tip of Luer part (52) and the outside surface of main body (41). Therefore, when outside surface (41a) of main body (41) is pushed in to about the same height position as the top of tapered part (13c) (where it connects with cylindrical part (13d)) by Luer part (52), depression (S) connects to the channel space in third branch channel (13a). The liquid medicine from Luer part (52) is then supplied to groove-shaped depression (S) and continues flowing into third branch channel (13a) from depression (S). In this way, coinjection from third branch channel (13a) is accomplished. Here, the region of outside surface (41a) where depression (S) is formed corresponds to the connecting surface in embodiments of the present invention.

When Luer part (52) is pulled out from where depression (S) connects to third branch channel (13a), the pushing force (Fa) from Luer part (52) is cancelled, and for this reason forces (Fg1) and (Fg2) also no longer act, and inner slit (41d)

closes. Along with this, only lifting forces (Fb1) and (Fb2) from first and second support arms (42a) and (42b) act on main body (41). Therefore, main body (41) is raised by the two support arms (42a) and (42b) and returns to the original position as shown in FIGS. 7 (a) and 8 (a). At this stage, outside surface (41a) of main body (41) is not connected to third branch channel (13a). And since main body (41) blocks opening (13b) of third branch tube (13) in leakproof fashion, third branch channel (13a) is cut off from the outside.

As explained above, three-way stopcock (100) in this embodiment is constituted such that valve member (40) installed in opening (13b) of third branch tube (13) of housing (10) is provided with a main body (41), and with a first support arm (42a) and second support arm (42b) as support parts, and such that outside surface (41a) of main body (41) connects to third branch channel (13a) when main body (41) is pushed into the channel space in third branch channel (13a) by a Luer part. Therefore, the Luer part is pushed into the channel space in third branch channel (13a) along with main body (41) by virtue of outside surface (41a) of main body (41) being pushed in from the outside by the Luer part of a syringe, and thus the Luer part connects to third branch channel (13a). If a liquid to be supplied from the Luer part is introduced at this stage, the introduced liquid flows into third branch channel (13a) from outside surface (41a). Supplying the liquid is accomplished in this way.

If the Luer part is separated from outside surface (41a) of main body (41) to cancel the pushing force, main body (41) returns to its original state (not pushed into third branch channel (13a)) by the lifting force (elastic force) received from first support arm (42a) and second support arm (42b). In the original state, main body (41) blocks opening (13b) of third branch tube (13) in leakproof fashion, so that third branch channel (13a) is cut off from the outside. In this way, three-way stopcock (100) in this embodiment is a system wherein main body (41) is pushed into the channel space by a pushing force (pressure) from the outside, and outside surface (41a) itself of main body (41) connects to the channel space, which is different from a system wherein the outside and the channel space are connected via a slit passing through the valve member as in the past. Thus, a conventional through slit formed in the valve member is not required. For this reason, the valve member can be prevented from becoming half open due to deterioration of the slit, and it is possible to realize a three-way stopcock that is reliably cut off from the outside when not in use and wherein there is little risk of leakage or bacterial growth.

Also, main body (41) and support parts (first support arm (42a) and second support arm (42b)) are formed integrally as a rubber member in this embodiment. Therefore, valve member (40) can be molded simply.

Furthermore, main body (41) of valve member (40) in this embodiment is shaped as a round columnar rubber plug with outside surface (41a) and inside surface (41b) as the end surfaces. With such a shape, side circumferential surface (41c) can be brought into contact over a broad area with the inside circumferential surface of tubular part (13d) joined to opening (13b) of third branch tube (13), and the fluid tightness of third branch channel (13a) can be sufficiently ensured.

Also, with this embodiment there is an opening (41d1) open to the inside surface (41b) in main body (41), and an inner slit (41d) is formed extending from inside surface (41b) toward outside surface (41a). The inner slit (41d) opens due to the force couple produced by the pushing force of the Luer part and the lifting force from first and second support arms (42a) and (42b). A depression (S) is formed in outside surface (41a) in a position corresponding to inner slit (41d) by the opening of inner slit (41d). The depression (S) is formed between the tip of the Luer part and outside surface (41a), so liquid to be coinjected from the Luer part can flow reliably into third branch channel (13a) via depression (S).

Furthermore, first support arm (42a) and second support arm (42b) are each formed in symmetrical portions relative to main body (41) in this embodiment. For this reason, the lifting force generated by the two support parts acts equally on main body (41), so that the pushing force and the lifting force are balanced. Thus, this balance will not be broken so that the main body can be prevented from tilting when pressed in.

Also, with this embodiment, inner slit (41d) is formed to divide inside surface (41b) of main body (41) into two parts. When formed in this way, inner slit (41d) is easily opened by the force couple. Depression (S) formed in outside surface (41a) of main body (41) when inner slit (41d) is open is in the form of a groove following opening (41d1) of inner slit (41d) formed in inside surface (41b). Thus the groove-shaped depressed portion acts as a channel, and liquid to be supplied can flow into third branch channel (13a) along the groove-shaped depression. Since the liquid to be supplied flows along the groove-shaped depression, the liquid will not overflow from the outside surface, and supplying the liquid can be accomplished more efficiently.

Second Embodiment

Next, a second embodiment of the present invention will be explained. This is characterized in that outer slits are furnished in the main body of the valve member. In other aspects, the form is the same as the aforementioned first embodiment. Note that in the embodiment below, the same symbols are assigned to features that are the same as these in the embodiment already explained, for which concrete explanations are omitted. The explanation concentrates on the portions that are different.

Figure 10:
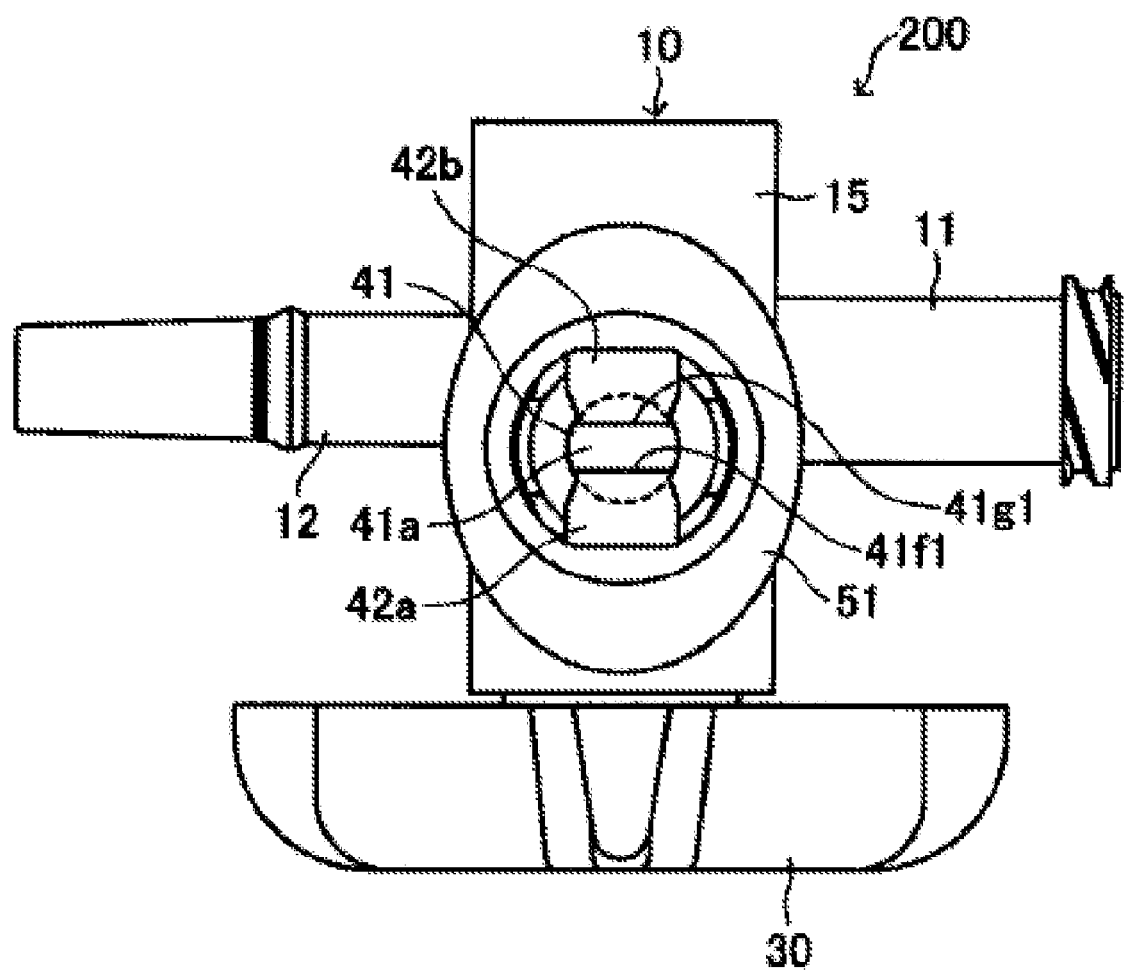
FIG. 10 is a plan view of a three-way stopcock pertaining to a second embodiment of the present invention.
Figure 11:
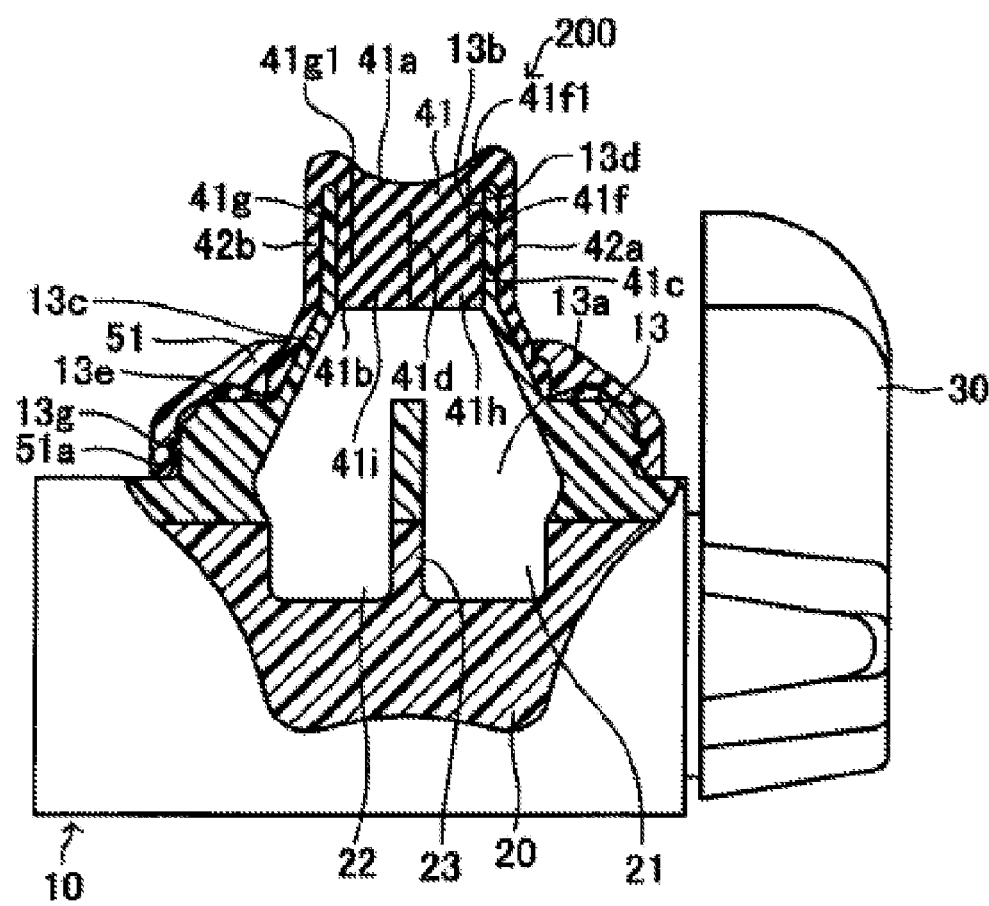
FIG. 11 is a partial side cross section of a three-way stopcock pertaining to the second embodiment of the present invention.

FIG. 10 is a plan view of a three-way stopcock in this embodiment, and FIG. 11 is a partial side cross section. Note that FIG. 11 corresponds to FIG. 4 in the first embodiment. As can be seen from the figures, in three-way stopcock (200) in this embodiment, a first outer slit (41f) and a second outer slit (41g) are formed in main body (41) of valve member (40). First outer slit (41f) has an opening (41f1) in outside surface (41a) of main body (41) near where first support arm (42a) is attached, and is formed to sag [open] toward inside surface (41b) from the opening (41f1). Second outer slit (41g) has an opening (41g1) that opens in outside surface (41a) near where second support arm (42b) is attached, and is formed to sag toward inside surface (41b) from the opening (41g1). Here, first outer slit (41f) and second outer slit (41g) do not reach inside surface (41b) and are not formed to pass through from outside surface (41a) to inside surface (41b).

As can be seen from FIG. 10, opening (41f1) of first outer slit (41f), and opening (41g1) of second outer slit (41g) formed in the outside surface of main body (41) are formed from edge to edge of outside surface (41a) to divide outside surface (41a). Therefore, outside surface (41a) of main body (41) is divided into three parts by opening (41f1) of first outer slit (41f) and opening (41g1) of second outer slit (41g). The openings (41f1) and (41g1) are also formed parallel to each other.

In addition, as shown in FIG. 11, first outer slit (41f) and second outer slit (41g) are formed parallel to inner slit (41d) that opens into inside surface (41b) of main body (41). And with this embodiment, first outer slit (41f) and second outer slit (41g) are formed in main body (41) to have plane symmetry when the plane in which inner slit (41d) is formed serves as the plane of symmetry. Note that with the exception of first outer slit (41f) and second outer slit (41g), this embodiment is constituted the same as the previous embodiment, so that the same portions are assigned the same symbols, and concrete explanations of them are omitted.

Figure 12A:
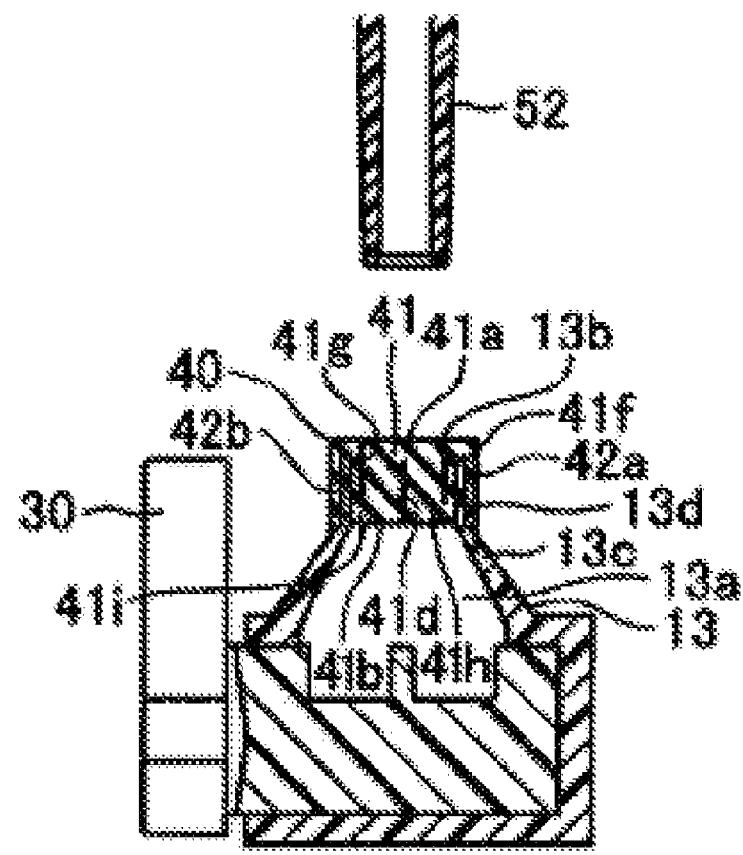
FIG. 12 shows the operation when coinjecting from the third branch tube of the three-way stopcock pertaining to the second embodiment of the present invention; (a) shows the situation the situation before the Luer part is inserted into the valve member, (b) when the Luer part is inserted in the valve member but the valve member is still closed, and (c) when the Luer part is inserted into the valve member and the valve member is open.
Figure 12B:
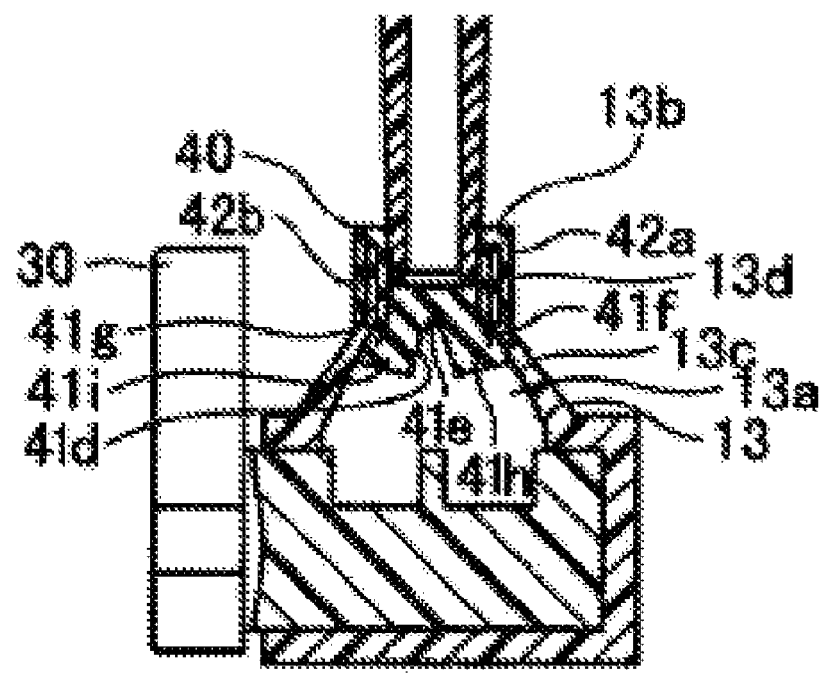
Figure 12C:
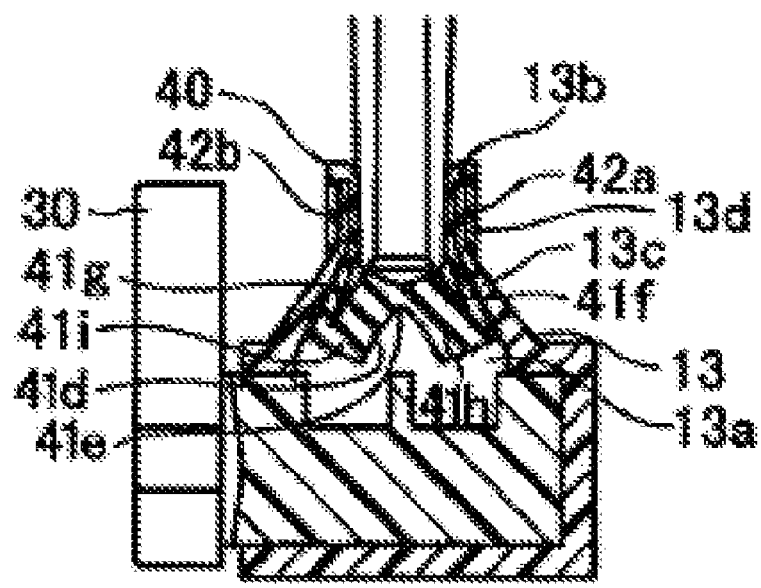
Figure 13A:
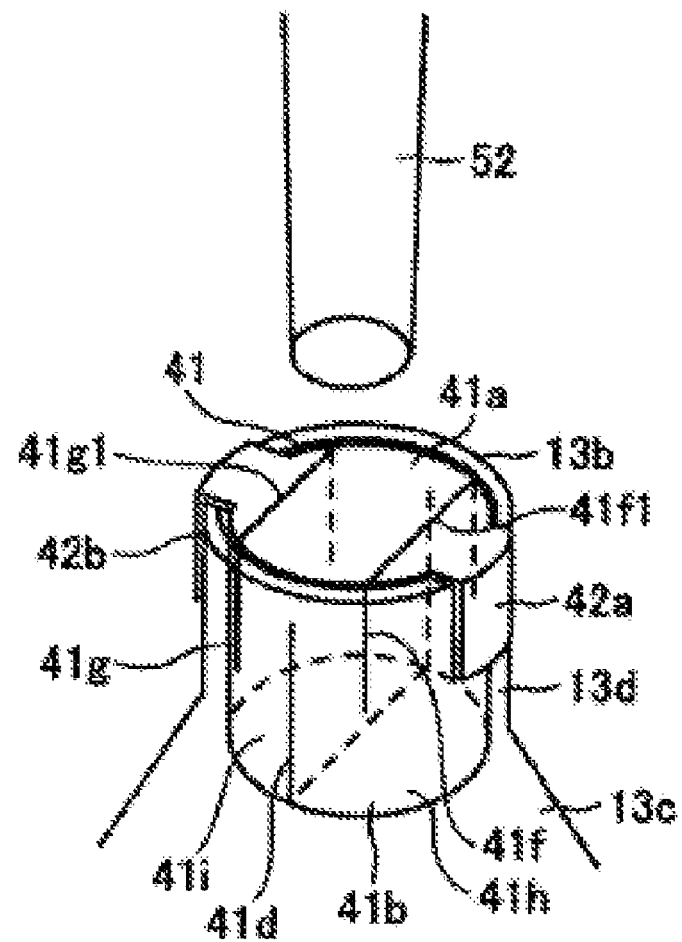
FIG. 13 shows the same operation as in FIG. 12 obliquely.
Figure 13B:
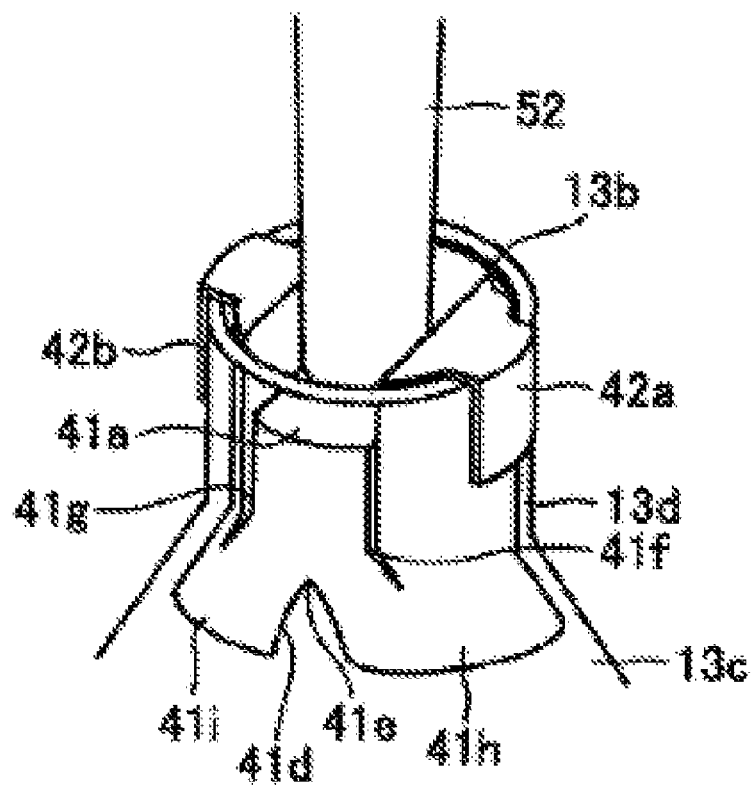
Figure 13C:
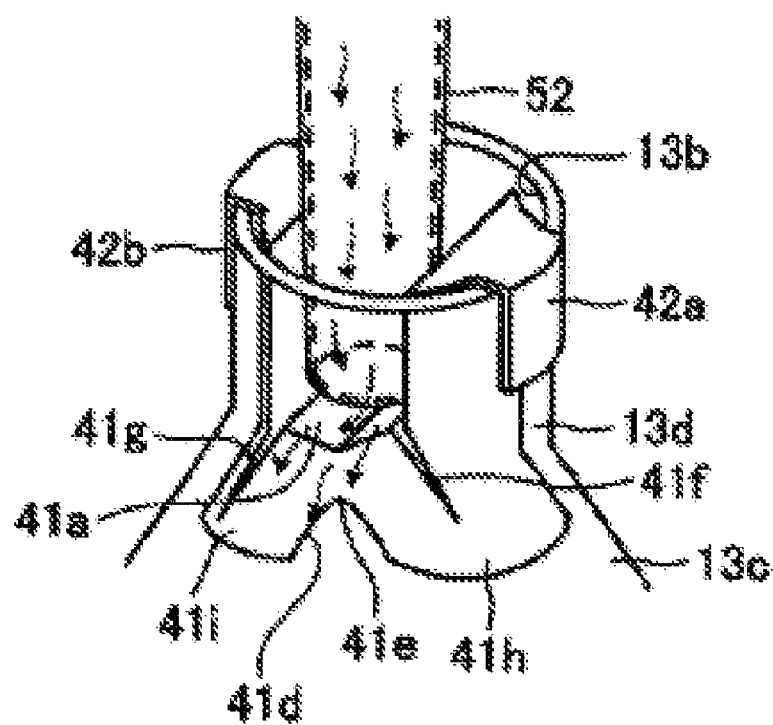

Next, a case will be explained in which a liquid medicine is coinjected from third branch tube (13) using three-way stopcock (200) with the aforementioned constitution. FIGS. 12 (a)-(c) schematically represent the operation up to when syringe Luer part (52) is installed in valve member (40) attached to opening (13b) of third branch tube (13) and liquid medicine is supplied from the syringe, and FIGS. 13 (a)-(c) represent the states in FIGS. 11 [sic; 12] (a)-(c) obliquely. FIGS. 12 (a) and 13 (a) represent the situation before Luer part (52) is inserted into valve member (40), FIGS. 12 (b) and 13 (b) that when Luer part (52) is inserted into valve member (40) but valve member (40) is still closed, and FIGS. 12 (c) and 13 (c) that when Luer part (52) is inserted into valve member (40) and valve member (40) is open, respectively.

First, as shown in FIGS. 12 (a) and 13 (a), the tip of Luer part (52) of a syringe filled with a liquid to be coinjected is brought close to valve member (40) installed in opening (13b) of third branch tube (13). Then, as shown in FIGS. 12 (b) and 13 (b), the tip of Luer part (52) is pushed against the outside surface (41a) of main body (41) of valve member (40), and the outside surface (41a) is pushed in toward third branch channel (13a) positioned toward the bottom in the figure. Here, in this embodiment, main body (41) of valve member (40), first support arm (42a) and second support arm (42b) are formed integrally of a rubber-like material. Therefore, main body (41) is pushed in downward in the figure and first support arm (42a) and second support arm (42b) are stretched by the pushing force of Luer part (52).

When first and second support arms (42a) and (42b) are stretched, the restoring elastic force from the support arms (42a) and (42b) acts on main body (41), and because support arms (42a) and (42b) attempt to return main body (41) to its original position, force that tries to raise main body (41) (lifting force) is generated. In this case, a force couple acts on main body (41), as explained for the first embodiment, from the pushing force and the lifting force. Inner slit (41d) opens as shown due to the force couple, and first portion (41h) and second portion (41i), divided by inner slit (41d), separate at the bottom in the figure.

When inner slit (41d) opens, base portion (41e) of inner slit (41d) is pushed downward in the figure. Then, pulled along by this, outside surface (41a) of main body (41) is also forced downward, and as shown in FIGS. 12 (c) and 13 (c), a depression (S) is formed near the center. Depression (S) is formed a groove (41d) running from the edge of outside surface (41a). Depression (S) is also formed between the open part at the tip of Luer part (52) and the outside surface of main body (41). Therefore, when outside surface (41a) of main body (41) is pushed in to about the same height position as the top of tapered part (13c) (where it connects with cylindrical part (13d)) by Luer part (52), depression (S) connects to the channel space in third branch channel (13a). The liquid medicine from Luer part (52) is then supplied to groove-shaped depression (S) and continues flowing into third branch channel (13a) from depression (S). In this way, coinjection from third branch channel (13a) is accomplished. Here, the region of outside surface (41a) where depression (S) is formed corresponds to the connecting surface in embodiments of the present invention.

Figure 14:
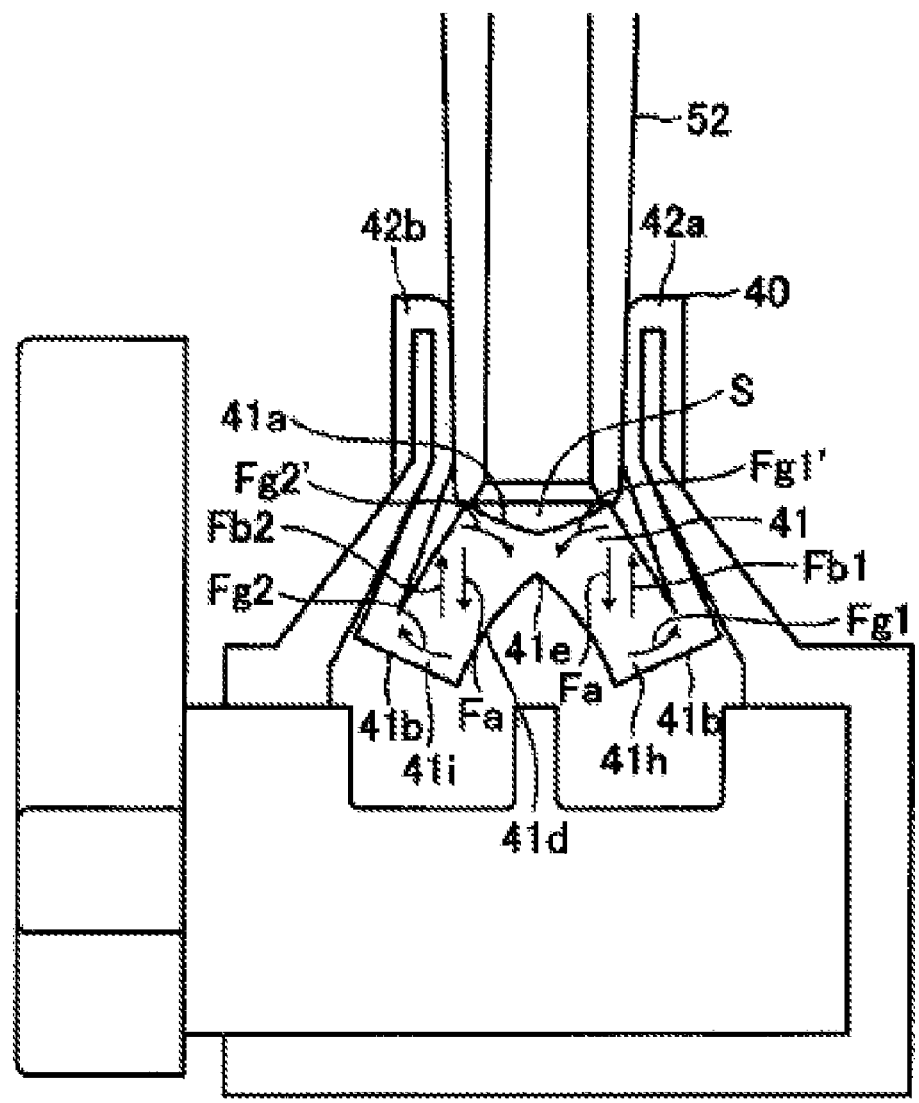
FIG. 14 pertains to the second embodiment of the present invention and shows the relationship between the pushing force and the lifting force acting on the main body of the valve member.

FIG. 14 shows the relationship between the pushing force from Luer part (52) and the lifting force from first and second support arms (42a) and (42b). As shown in FIG. 14, pushing force (Fa) that the open part at the tip of Luer part (52) applies to main body (41) of valve member (40) acts in a direction (downward in the figure) to push main body (41) toward third branch channel (13a). In contrast to this, lifting force (Fb1) that first support arm (42a) applies to main body (41) acts in a direction to raise main body (41) from third branch channel (13a) to the outside (upward in the figure). In the same way, lifting force (Fb2) that second support arm (42b) applies to main body (41) also acts in a direction to raise main body (41) from third branch channel (13a) to the outside (upward in the figure). Pushing force (Fa) and lifting forces (Fb1) and (Fb2) act in opposite directions from different positions, so a force couple acts on main body (41).

As explained relative to the first embodiment, the center of main body (41) is pushed in toward third branch channel (13a) and the region near the outer circumferential edge is lifted by support arms (42a) and (42b) by the force couple acting on main body (41). In such a state, the inside surface (41b) side of main body (41) is subjected to a force acting to pull from the center toward the outer circumference, as indicated by arrows (Fg1) and (Fg2) in the figure. Because of this, inner slit (41d) opens, and first portion (41h) and second portion (41i) divided by inner slit (41d) separate in the region toward the bottom in the figure.

On the other hand, the outside surface (41a) side of main body (41) is subjected to a force acting in a direction to cause it to fold inward, as indicated by arrows (Fg1') and (Fg2') in the figure. In this case, since first support arm (42a) and second support arm (42b) are attached to the edge of outside surface (41a) of main body (41), the regions near the base ends of the support arms are subjected to stress by the force acting in the directions indicated by arrows (Fg1') and (Fg2').

In this embodiment, first outer slit (41f) is formed near the where first support arm (42a) is attached, and second inner slit (41g) near where second support arm (42b) is attached. For this reason, force acting on these regions is received due to slits (42f) and (42g) [sic; (41f) and (41g)] opening. Thus, the concentration of stress near there can be moderated. In this way, with this embodiment, stress concentration acting on the outside surface (41a) side of main body (41) can be moderated, the reliability of the valve member can be improved, and the valve member will also have a longer life.

From the stage shown in FIG. 12 (c), 13 (c) or 14, when Luer part (52) is pulled out, the pushing force (Fa) from Luer part (52) is cancelled. Because of this, forces (Fg1), (Fg2), (Fg1') and (Fg2') also no longer act, and inner slit (41d), first outer slit (41f) and second outer slit (41g) close. Here, only lifting forces (Fb1) and (Fb2) from first and second support arms (42a) and (42b) act on main body (41). Therefore, main body (41) is lifted by the two support arms (42a) and (42b) and returns to its original position as shown in FIGS. 12 (a) and 13 (a). At this stage, outside surface (41a) of main body (41) is not connected to the channel space in third branch channel (13a). Because main body (41) is installed in opening (13b) of third branch tube (13) in leakproof fashion, the channel space in third branch channel (13a) is cut off from the outside.

Third Embodiment

Next, a third embodiment of the present invention will be explained. This embodiment is characterized in that the connector is applied to a coinjection appliance for coinjecting a liquid midway along a channel, rather than to a three-way stopcock. In other aspects, it has the same form as the aforementioned first embodiment.

Figure 15A:
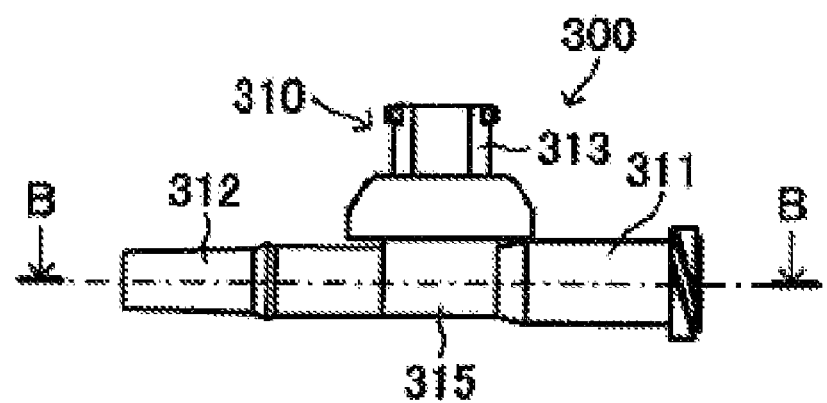
FIG. 15 shows a coinjection appliance pertaining to a third embodiment of the present invention; (a) is a front view, (b) a plan view and (c) a side view.
Figure 15B:
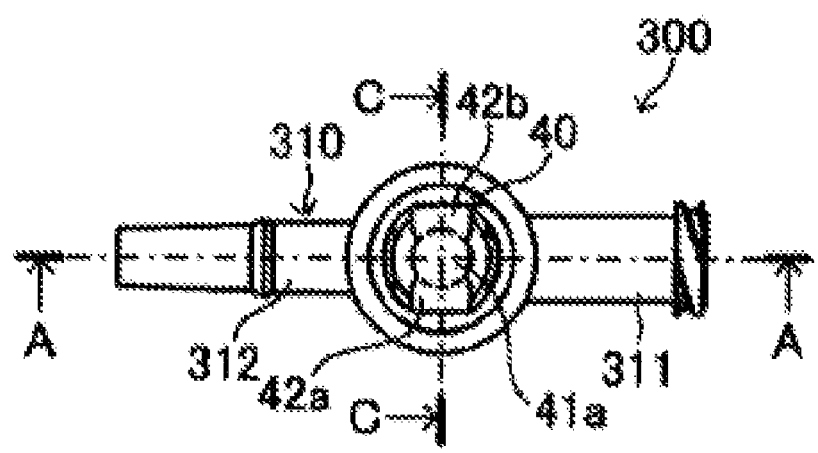
Figure 15C:
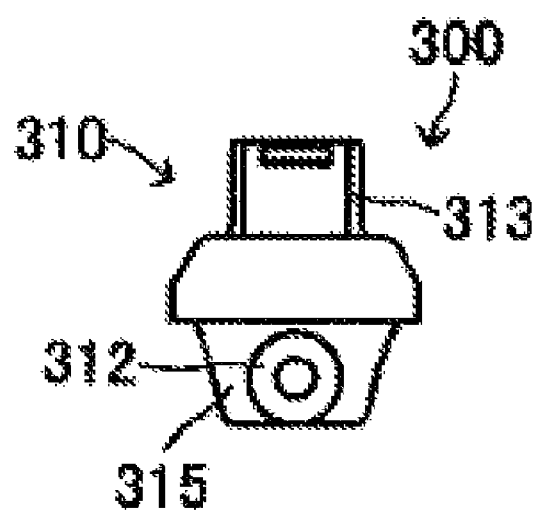
Figure 16A:
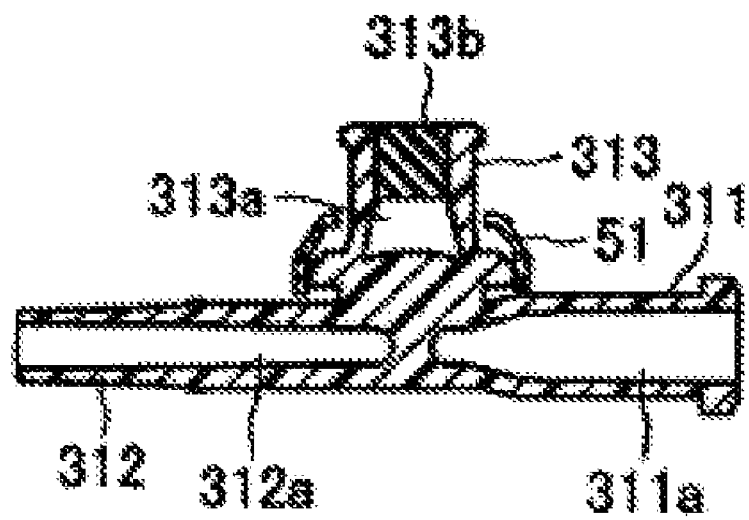
FIG. 16 is a cross section of the coinjection appliance pertaining to the third embodiment of the present invention; (a) is cross section A-A in FIG. 15 (*b*), (b) cross section B-B in FIG. 15 (*a*), and (c) cross section C-C in FIG. 15 (*b*).
Figure 16B:
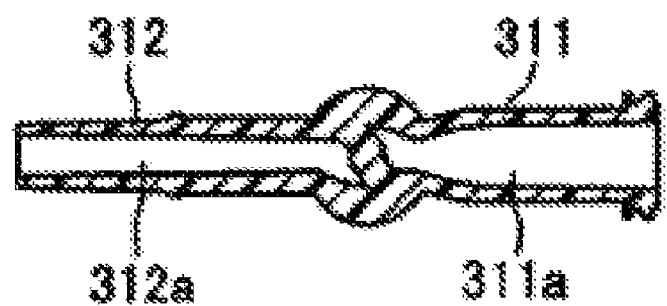
Figure 16C:
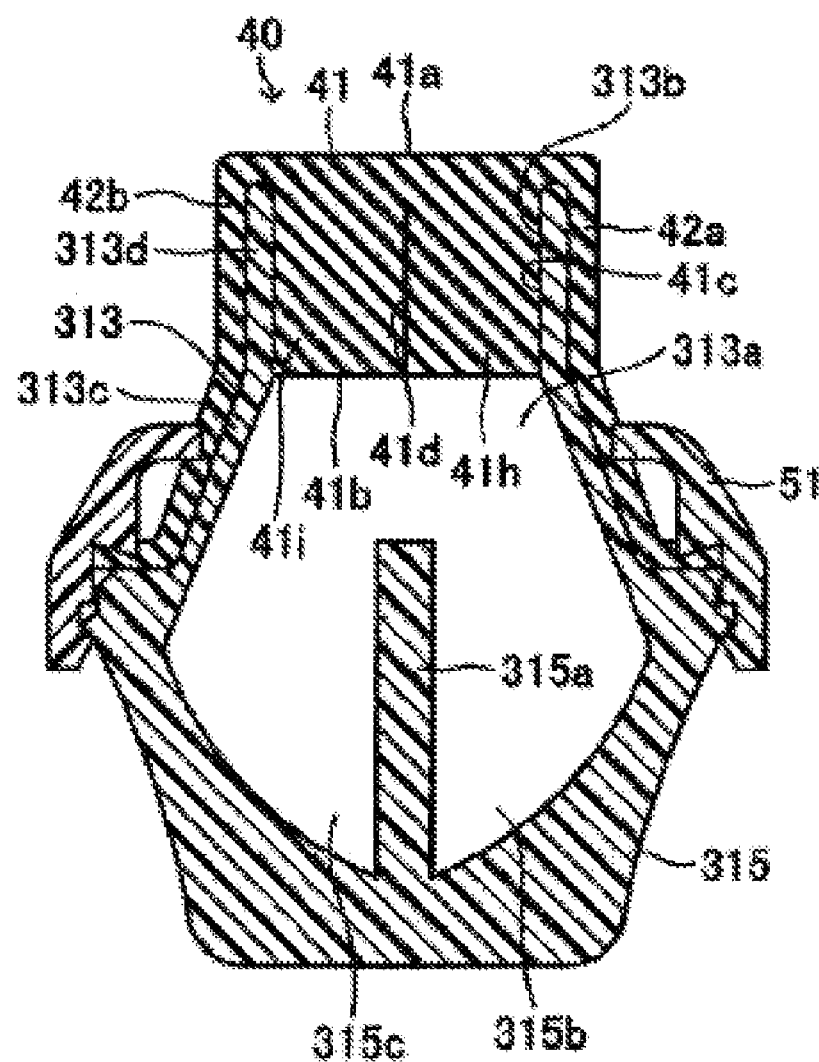

FIG. 15 (*a*) is a front view of the coinjection appliance in this embodiment, FIG. 15 (*b*) is a plan view, and FIG. 15 (*c*) is a side view. FIG. 16 (*a*) is cross section A-A in FIG. 15 (*b*), FIG. 16 (*b*) cross section B-B in FIG. 15 (*a*), and FIG. 16 (*c*) cross section C-C in FIG. 15 (*b*).

As can be seen from the figures, coinjection appliance (300) is provided with a housing (310). Housing (310) is provided with a first branch tube (311), a second branch tube (312), a third branch tube (313), and a central confluence part (315), and each branch tube is connected to the central confluence part (315). Branch channels (first branch channel (311*a*), second branch channel (312*a*) and third branch channel (313*a*)) are respectively formed in each of the branch tubes. As can be seen from FIG. 16 (*c*), a partition (315*a*) is formed in central confluence part (315), and the interior space in central confluence part (315) is divided into a first connecting space (315*b*) and a second connecting space (315*c*) by partition (315*a*). Here, first connecting space (315*b*) and second connecting space (315*c*) can be connected through a third branch channel (313*a*) positioned at the top of partition (315*a*) in the figure.

First connecting space (315*b*) is also connected with first branch channel (311*a*), and second connecting space (315*c*) is connected with second branch channel (312*a*). Therefore, first branch channel (311*a*) is connected with second branch channel (312*a*) through first connecting space (315*b*) and second connecting space (315*c*).

As shown in FIGS. 15 (*a*) and 16 (*a*), first branch tube (311), second branch tube (312) and third branch tube (313) are each connected to central confluence part (315) at intervals of approximately 90 degrees. First branch tube (311) and second branch tube (312) are arranged facing each other. Third branch tube (313) is positioned separated from both first branch tube (311) and second branch tube (312) at an interval of 90 degrees.

As shown in FIG. 16 (*c*), third branch tube (313) is constituted with a tapered part (313*c*) that has a tapered inner wall, and cylindrical part (313*d*) extending upward in the figure from the tip of tapered part (313*c*). An opening (313*b*) is also formed at the tip of cylindrical part (313*d*). A third branch channel (313*a*) is formed inside tapered part (313*c*). Third branch channel (313*a*) is connected to both first connecting space (315*b*) and second connecting space (315*c*) inside central confluence part (315). Note that the constitution is otherwise the same as in the aforementioned first embodiment, particularly the constitution of valve member (40), so the same features are represented by the same symbols, and concrete explanations of them are omitted.

In coinjection appliance (300) in this embodiment constituted as described above, liquid medicine is supplied from a liquid medicine tube connected to first branch tube (311). The liquid medicine then flows into first connecting space (315*b*) of central confluence part (315) from first branch channel (311*a*). The liquid medicine in first connecting space (315*b*) passes over partition (315*a*) and enters third branch channel (313*a*). The liquid medicine passes beyond partition (315*a*) from the inside of third branch channel (313*a*) and enters second connecting space (315*c*) formed on the side opposite from first connecting space (315*b*). It then flows into second branch channel (312*a*) from second connecting space (315*c*). The main channel flow is formed in this way.

Here, opening (313*b*) of third branch tube (313) as shown in FIG. 16 (*c*) is blocked in leakproof fashion by main body (41) of valve member (40), and is closed. Therefore, the main channel flow circulating as described above will not leak out of third branch tube (313). Also, no impurities will get into third branch channel (313*a*) from the outside through opening (313*b*) of third branch tube (313).

When a liquid medicine is coinjected from third branch tube (313), a syringe Luer part is inserted into main body (41) of valve member (40). Then main body (41) of valve member (40) is pushed into third branch channel (313*a*) by the Luer part, and valve member (40) is opened. The operation when valve member (40) is opened and the principle whereby outside surface (41*a*) of main body (41) connects to third branch channel (313*a*) are the same as was explained for the aforementioned first embodiment, so they are omitted here. In this way, embodiments of the present invention can also be applied to a coinjection appliance.

Fourth Embodiment

Next, a fourth embodiment of the present invention will be explained. This embodiment is characterized in that the connector is applied as a connector that is attached to the end part of a channel, the channel is normally closed, and the channel is opened when a tube or syringe Luer part is attached. In other aspects, it has the same form as the aforementioned first embodiment.

Figure 17A:
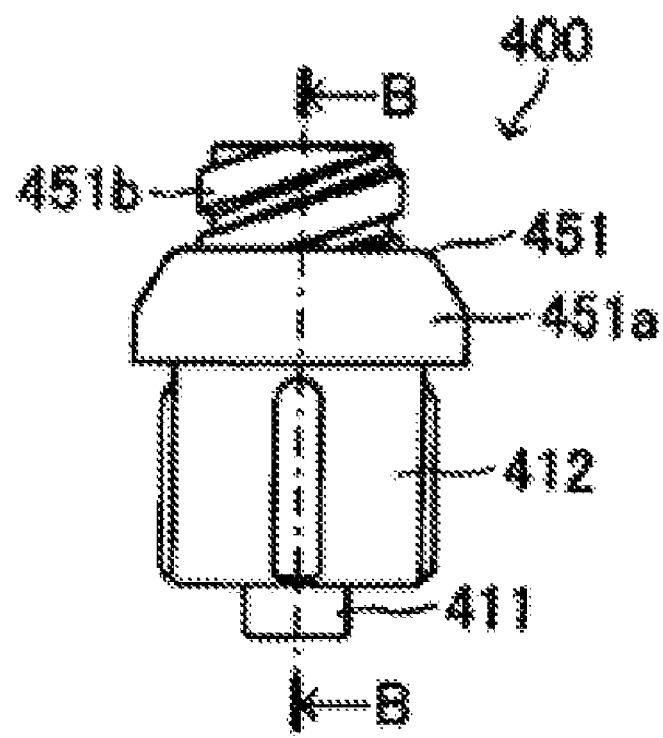
FIG. 17 shows a connector pertaining to a fourth embodiment of the present invention; (a) is a front view, (b) a side view, and (c) a plan view.
Figure 17B:
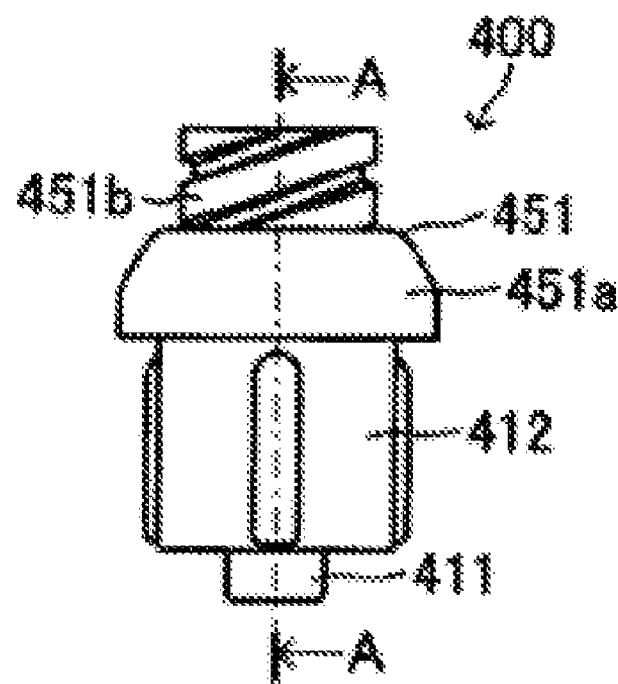
Figure 17C:
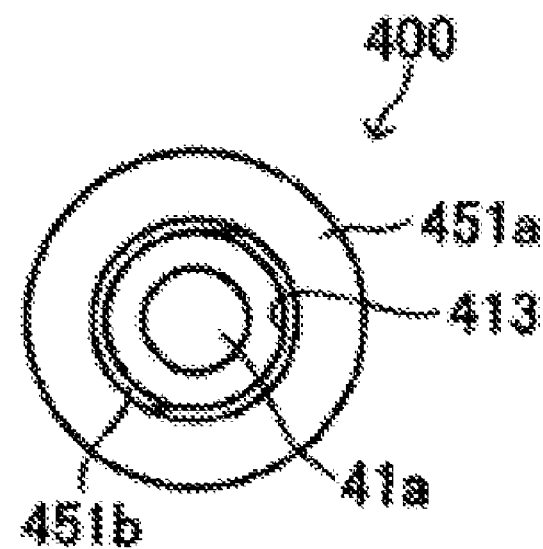
Figure 18A:
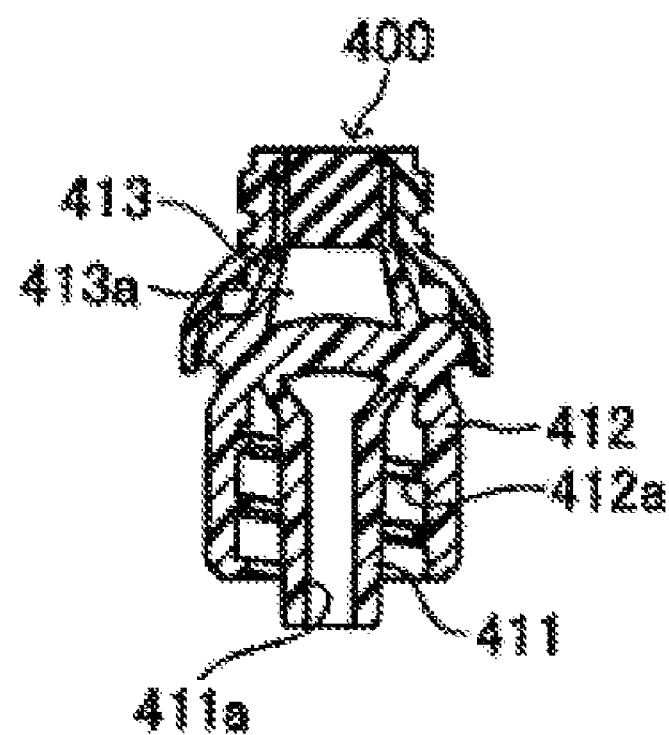
FIG. 18 is a cross section of the connector pertaining to the fourth embodiment of the present invention; (a) is cross section A-A in FIG. 17 (*b*), and (b) is cross section B-B in FIG. 17 (*a*).
Figure 18B:
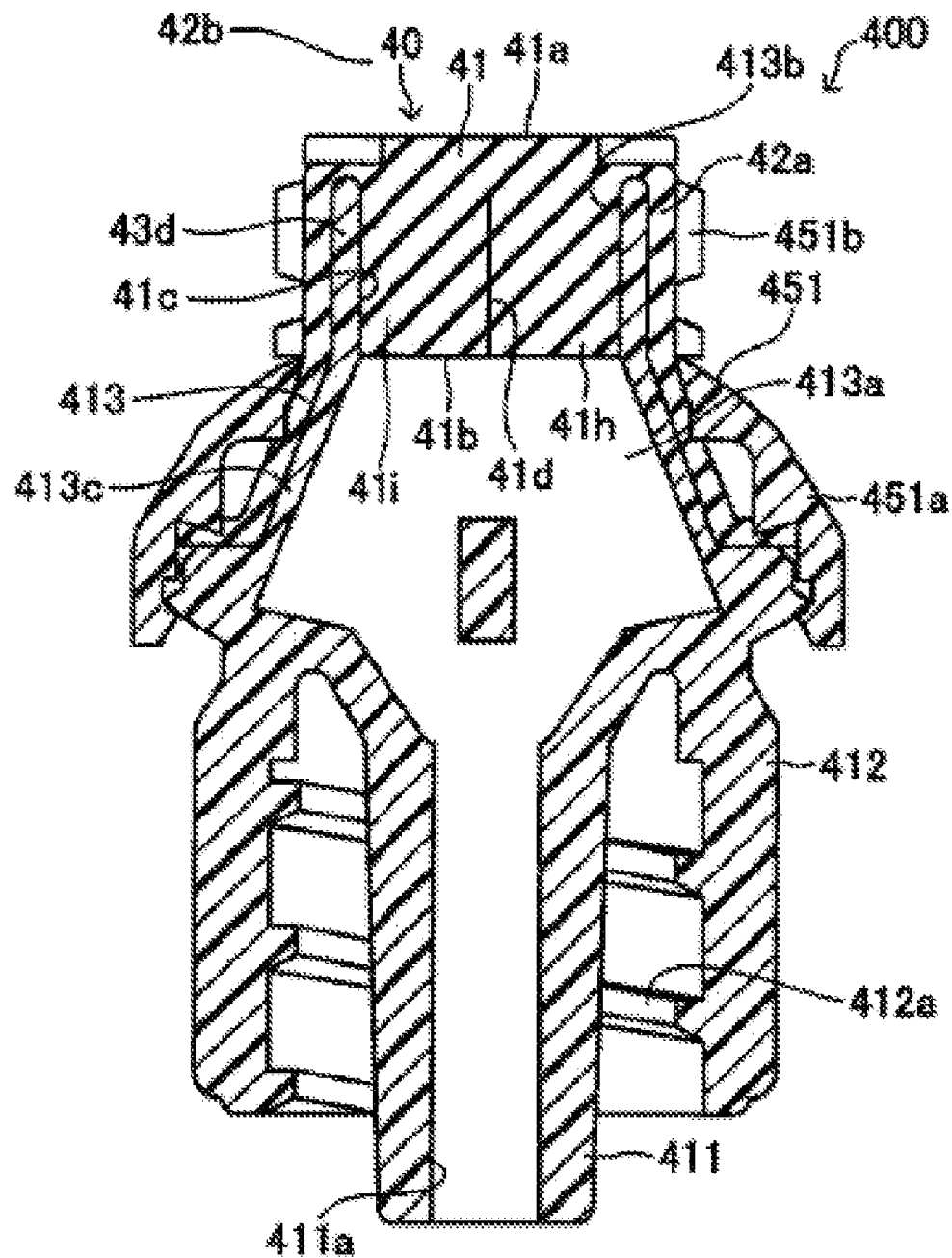

FIG. 17 (*a*) is a front view of the connector in this embodiment, FIG. 17 (*b*) a side view, and FIG. 17 (*c*) a plan view. FIG. 18 (*a*) is cross section A-A in FIG. 17 (*b*), and FIG. 18 (*b*) is cross section B-B in FIG. 17 (*a*).

As can be seen from the figures, connector (400) in this embodiment is provided with a housing (410). A connection tube part (411), a connection tube cover part (412) and a tube connection part (413) are formed in housing (410).

Connection tube part (411) has a long, narrow cylindrical shape, and a connection channel (411*a*) is formed inside it. A tubular body, such as a tube, is connected to connection tube part (411). Connection tube cover part (412) is formed cylindrically to cover the outer circumference of connection tube part (411). Inside threads (412*a*) are formed in the inner wall of connection tube part (412). Inner threads (412*a*) screw onto a tube connected to connection tube part (411) and are used to attach the tube. Tube connection part (413) is coupled to the base end of connection tube part (411), and a connecting space (413*a*) is formed on the inside. Connecting space (413*a*) is connected to connection channel (411*a*) in connection tube part (411), as shown in the figures. Note that connecting space (413*a*) corresponds to the channel space in embodiments of the present invention.

As shown in FIG. 18 (*b*), tube connection part (413) is constituted with a tapered part (413*c*) that has a tapered inner wall, and a cylindrical part (413*d*) extending upward in the figure from the tip of tapered part (413*c*). An opening (413*b*) is also formed at the tip of cylindrical part (413*d*). A connecting space (413*a*) is formed on the inside of tapered part (413*c*). Connecting space (413*a*), as described above, is connected to connection channel (411*a*) positioned in the lower portion.

A cover (451) made of plastic is attached around the outer circumference of tube connection part (413). Cover (451) has a dome-shaped part (451*a*) and an outer threaded part (451*b*) running vertically from the center part of dome part (451*a*). The top end of outer threaded part (451*b*) in the figure is open, and cylindrical part (413*d*) of tube connection part (413) is inserted through this opening, and cover (451) is installed on tube connection part (413). An annular groove is also formed in the inner circumference at the lower end of cover (451) in the figure. Cover (451) is attached to tube connection part (413) by this groove being engaged with tapered part (413*c*). Note that outer threads are formed in the outer wall of outer threaded part (451b). These outer threads allow screwing on the Luer part of a syringe or the like to lock it. Note that the constitution, particularly the constitution of valve member (40), is otherwise the same as the aforementioned first embodiment, so the same features are represented with the same symbols, and concrete explanations of them are omitted.

In connector (400) in this embodiment constituted as described above, a tubular body, such as a tube, is first connected to connection tube part (411), and the tube is affixed by screwing into the inner threads of connection tube cover part (412). In this case, when no syringe is attached to valve member (40), opening (413b) of tube connection part (413) is blocked in leakproof fashion by main body (41) of valve member (40) and is closed, as shown in FIG. 18 (b). Therefore, the tube attached to connection tube part (411) is blocked by valve member (40). Thus even when liquid has already flowed into the tube, it will not leak to the outside. Also, no impurities will get into connecting space (413a) from the outside through opening (413b) of tube connection part (413).

When it is desired to supply liquid medicine from tube connection part (413), the Luer part of a syringe is inserted into main body (41) of valve member (40), it is connected by screwing onto the outer threaded part, and the Luer part is attached. Then main body (41) is pushed into connecting space (413a) by the Luer part to open valve member (40). Note that the operation when valve member (40) is opened and the principle whereby outside surface (41a) of main body (41) connects to third branch channel (313a) [sic; connecting space (413a)] are the same as was explained for the first embodiment, so they are omitted here. In this way, embodiments of the present invention can also be applied to a connector as described above.

Fifth Embodiment

Next, a fifth embodiment of the present invention will be explained. This embodiment is characterized in that, the housing of a three-way stopcock is formed divided, and in that the divided housing is coupled in leakproof fashion by means of an elastic member. In other aspects, it has the same form as the aforementioned first embodiment.

Figure 19:
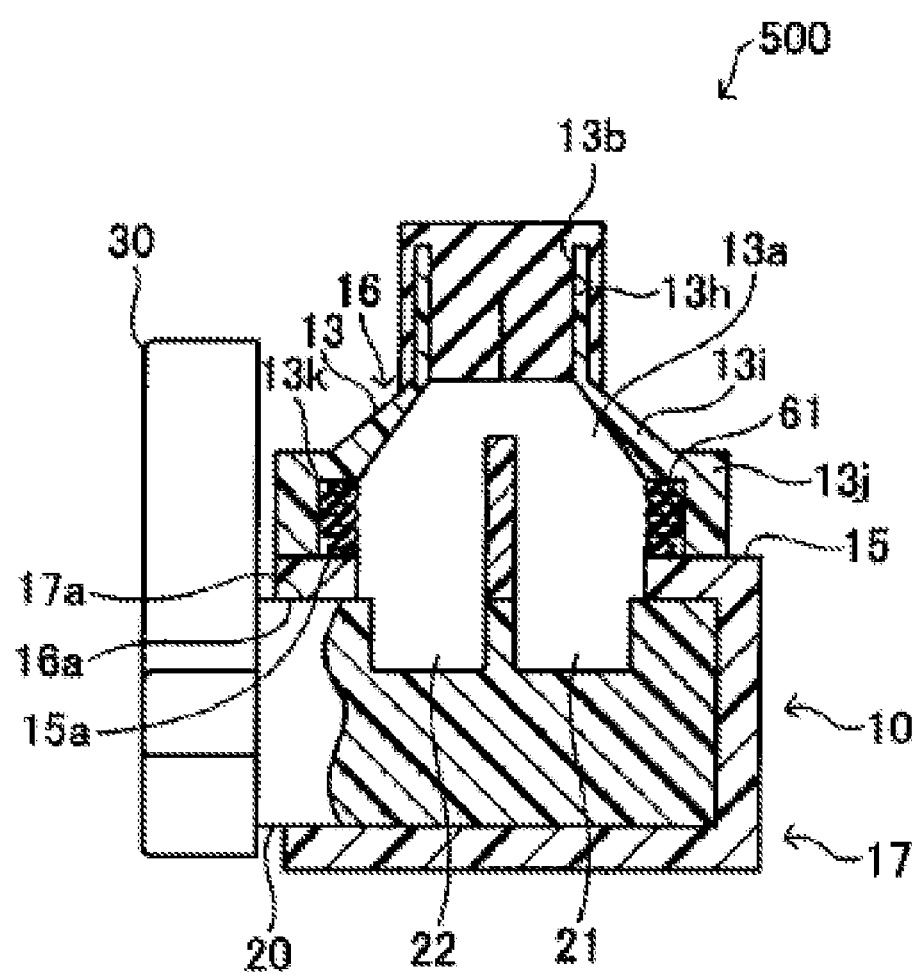
FIG. 19 is cross section A-A in FIG. 2 for a three-way stopcock pertaining to a fifth embodiment of the present invention.
Figure 20:
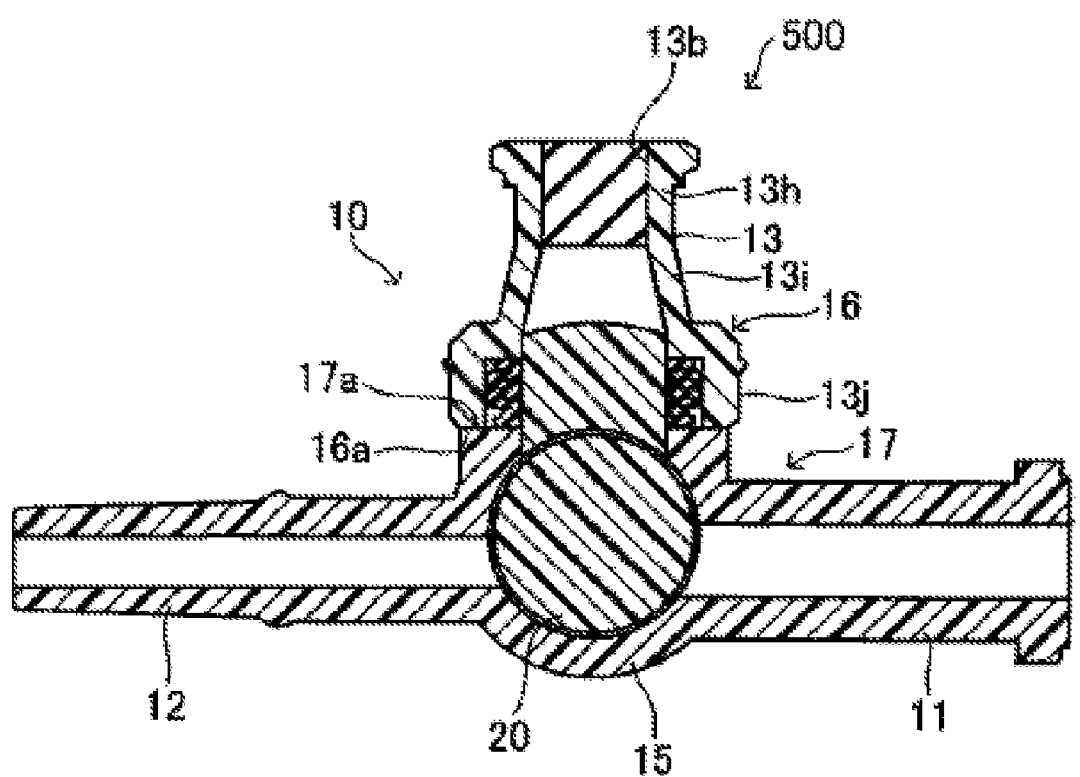
FIG. 20 is cross section B-B in FIG. 3 for the three-way stopcock pertaining to the fifth embodiment of the present invention.
Figure 21A:
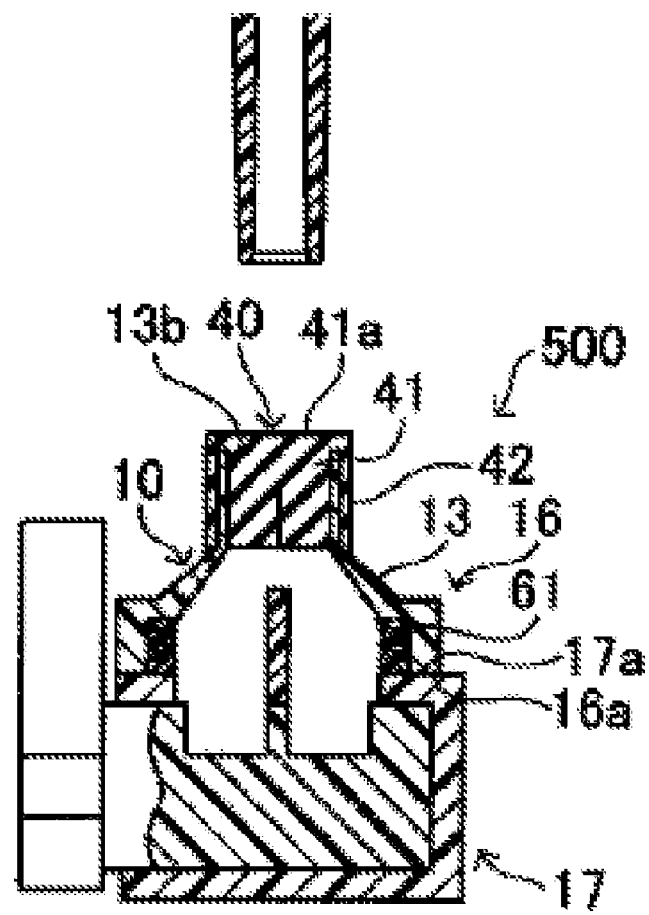
FIG. 21 shows the operation of the valve member of the three-way stopcock pertaining to the fifth embodiment of the present invention. (a) shows the situation before the Luer part is inserted, (b) when Luer part (52) has been inserted, (c) while Luer part (52) is being pulled out, and (d) after Luer part (52) has been pulled out.
Figure 21B:
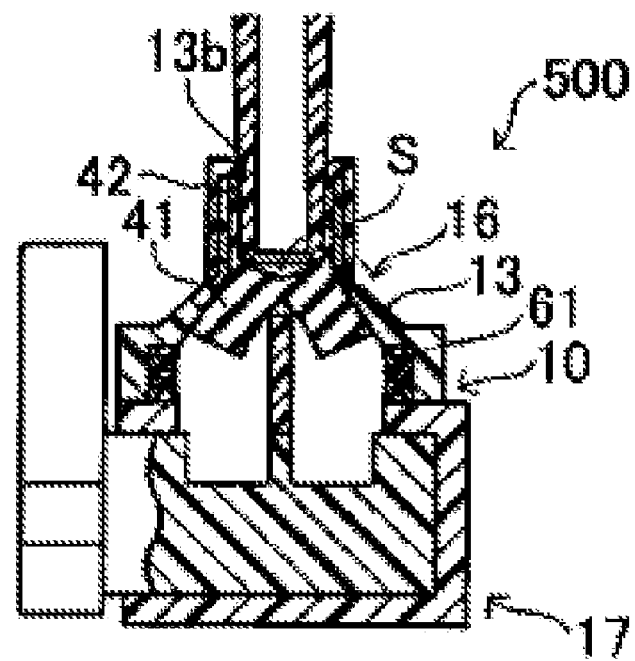
Figure 21C:
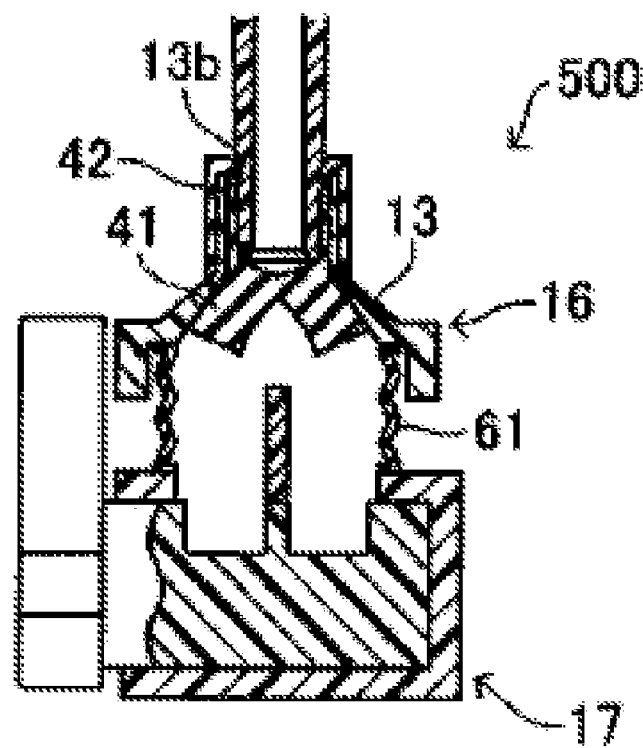
Figure 21D:
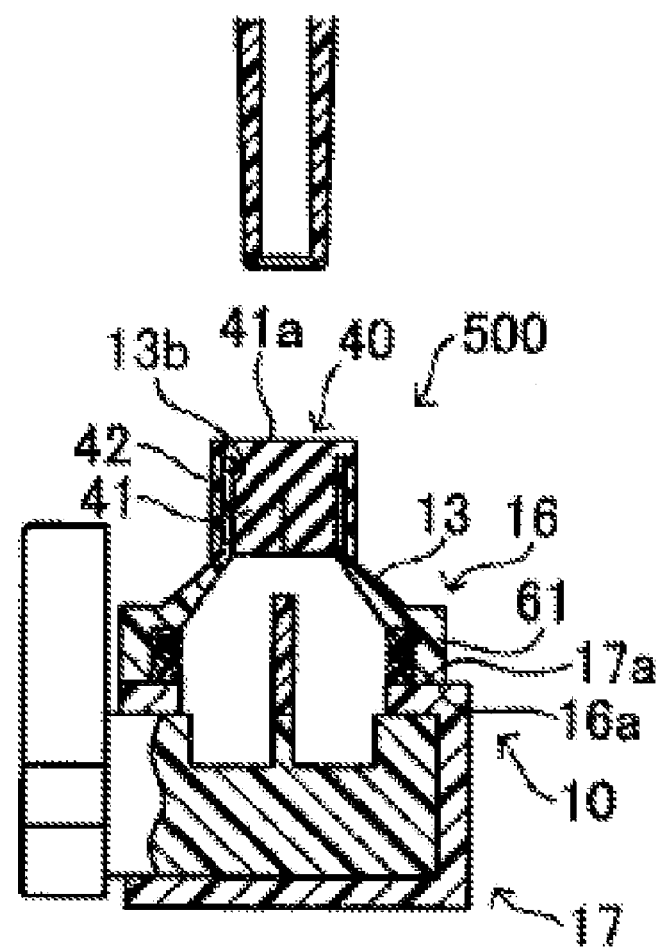

FIGS. 19 and 20 are cross sections of the three-way stopcock pertaining to this embodiment. Note that FIG. 19 corresponds to cross section A-A in FIG. 2, and FIG. 20 corresponds to cross section B-B in FIG. 3. As can be seen from the figures, with the three-way stopcock (500) in this embodiment, third branch tube (13) is formed separately from the other portions constituting the housing so that it can be separated from tubular part (15). Therefore, housing (10) is formed divided into a portion (16) that forms third branch tube (13), and a second portion (17) that forms first branch tube (11), second branch tube (12) and tubular part (15), which are the other portions.

Third branch tube (13) has a first cylindrical part (13h) in which is formed an opening (13b), opening upward in the figure, a tapered part (13i) having a tapered inner wall wherein the inner diameter becomes larger moving downward in the figure from the lower end of first cylindrical part (13h), and a second cylindrical part (13j) extending vertically and widening in diameter from the bottom of tapered part (13i) in the figure. The lower end of second cylindrical part (13j) is open, and the end surface in the opening serves as the dividing surface (16a) of first portion (16). On the other hand, the side peripheral part of cylindrical part (15) is open at the top, and the surface enclosing the opening serves as the dividing surface (17a) of second portion (17). Dividing surfaces (16a) and (17a) are facing, and first portion (16) and second portion (17) are combined to form housing (10) with the two surfaces touching. Inside housing (10) assembled in this way, the space inside third branch channel (13a) connects to spaces in grooves (21) and (22) formed in plug body (20) inside tubular part (15), and a channel space is formed by these spaces.

A bellows-shaped elastic member (61) formed with silicone rubber is attached along the inner circumference of second cylindrical part (13j). Elastic member (61) is cylindrical. One end is connected in leakproof fashion to side circumferential surface (15a) of cylindrical part (15) positioned on the inside of dividing surface (17a), and the other end is connected in leakproof fashion to the inner circumferential end surface (13k) formed inward in the radial direction at the upper end of second cylindrical part (13j). Because of this, third branch tube (13) and tubular part (15) are coupled in leakproof fashion by elastic member (61) so that liquid in the channel space will not leak outside through the gap formed between dividing surface (16a) of first portion (16) and dividing surface (17a) of second portion (17). In the state shown in the figure, elastic member (61) generates a contraction force in the axial direction. Therefore, dividing surface (16a) is pressed against dividing surface (17a) by the contraction force of elastic member (61), and first portion (16) and second portion (17) touch. Note that the constitution otherwise is the same as the aforementioned first embodiment, so a concrete explanation is omitted by invoking the explanation of the first embodiment.

FIG. 21 shows the situation when a Luer part (52) is inserted into opening (13b) of third branch tube (13), and that when the Luer part (52) that was inserted in opening (13b) is removed, in three-way stopcock (500) in this embodiment. (a) shows the situation the situation before Luer part (52) is inserted into opening (13b), (b) that when Luer part (52) has been inserted into opening (13b), (c) that while Luer part (52) is being pulled out of opening (13b), and (d) that after Luer part (52) has been pulled out of opening (13b).

From the stage shown in FIG. 21 (a), Luer part (52) is inserted into main body (41) of valve member (40) attached to opening (13b), and valve member (40) is opened as shown in FIG. 21 (b). Then the liquid is coinjected from Luer part (52) into the channel space from depressed part (S) formed in outside surface (41a) of main body (41). The operation of valve member (40) up to here is the same as that explained for the first embodiment, so that a concrete explanation of it is omitted by invoking the explanation of the first embodiment.

When Luer part (52) is pulled out of opening (13b), Luer part (52) is pulled vertically upward from the stage shown in FIG. 21 (b). Frictional force caused by the gripping force to which it is subjected from support arms (42) of valve member (40) is generated in the direction of removal in Luer member (52) at this time. This frictional force exceeds the contraction force of elastic member (61) at the start of pulling out of Luer part (52). For this reason, as Luer part (52) is pulled out as shown in FIG. 21 (c), first portion (16) that forms third branch tube (13) that grips Luer part (52) moves upward in the figure along with Luer part (52), and first portion (16) separates from second portion (17). Elastic member (61) connected to first portion (16) and second portion (17) stretches because of the aforementioned separation. The sectional area of the channel space formed in housing (10) also increases as shown in FIG. 21 (c) due to stretching of the elastic member (61), and the channel space capacity increases.

When Luer part (52) is pulled out to a certain extent, the contraction force of elastic member (61) increases to exceed the frictional force acting on Luer part (52). Luer part (52) is then pulled out of opening (13b) of third branch tube (13). When Luer part (52) is pulled out, first portion (16) moves closer to second portion (17) because of the contraction force of elastic member (61), and dividing surfaces (16a) and (17a) return to their original contract state. as shown in FIG. 21 (d). At this time, the channel space is decreased by the contraction of elastic member (61) from the state where the channel space was increased (state in FIG. 21 (c)), producing the state of return to the original volume (state in FIG. 21 (d)). For this reason, when Luer part (52) is pulled out of opening (13b) of third branch tube (13), the pressure in the channel space increases and the channel space becomes positively pressurized.

However, when a Luer part is inserted into a three-way stopcock or the like, the valve body attached to the tip of the Luer part or the three-way stopcock sometimes projects into the channel space, decreasing the volume of the channel space. When the Luer part is pulled out in such a state, the portion projecting into the channel space is withdrawn, returning it to the original state, so the volume of the channel space increases, the pressure in the channel space decreases, and the channel space becomes negatively pressurized. When the channel space is negatively pressurized when the Luer part is pulled out, there is the risk of liquid in a medical tube connected to the three-way stopcock flowing backward, so it is undesirable for the pressure in the channel space to become negative.

Concerning this point, when the Luer part is pulled out with this embodiment, while the channel space increases as shown in FIG. 21 (c) and pressure in the channel space decreases for the time being, the channel space ultimately returns to the original state as shown in FIG. 21 (d). The channel space volume at this time decreases and the pressure increases, so that the channel space becomes positively pressurized. Therefore, liquid in the medical tube connected to the three-way stopcock can be kept from flowing backward by the channel space becoming positively pressurized. Note that in this embodiment, at the time of the stage shown in FIG. 21 (c), the channel space volume increases, so the pressure in the channel space decreases and there is a risk of the inside of the channel space becoming negatively pressurized. At this time, the effect of the aforementioned negative pressure is kept to a minimum by the production of a forward flow in the main channel by liquid being supplied from Luer part (52), and the liquid in the medical tube connected to three-way stopcock (500) can circulate without interruption.

As described above, three-way stopcock (500) as the connector pertaining to this embodiment is provided with a housing (10) that has a third branch tube (13) in which is formed an opening (13b) open to the outside, and a first branch tube (11) and a second branch tube (12) as the connection openings connected to a tube body; inside the housing is formed a channel space through which liquid can flow through first branch tube (11) and second branch tube (12); and a valve member (40) is attached to opening (13b); whereby liquid can be supplied from the outside into the channel space by opening and closing said valve member (40). Valve member (40) is constituted in the same as in the aforementioned first embodiment, and it achieves the same effects as the aforementioned first embodiment.

Three-way stopcock (500) in this embodiment is also formed such that housing (10) is divided into a first portion (16) that has opening (13b) and a second portion (17) that has first branch tube (11) and second branch tube (12), and an elastic means (61) is elastically connected to first portion (16) and second portion (17) so that liquid in the channel space will not leak outside through the gap formed between dividing surface (16a) of first portion (16) and dividing surface (17a) of second portion (17). For this reason, the channel space can be positively pressurized when Luer part (52) is pulled out, and reverse flow of the liquid in the medical tube connected to the three-way stopcock can be prevented.

Note that it is obvious that a constitution wherein the channel space volume in housing (10) is reduced when Luer part (52) is pulled out of opening (13b), making the pressure in the channel space positive, such as is illustrated in this embodiment, can be applied not only to a three-way stopcock, but also to the coinjection appliance illustrated in the third embodiment, the connector illustrated in the fourth embodiment, etc.

For the avoidance of doubt, it is expressly indicated that the arrangement of the elastic means (61) may be incorporated into any of the embodiments described above, although for illustrational purposes it has only been described with reference to the fifth embodiment.

The system is such that a slit passing through it, as described above, is formed in the valve member used for a conventional closed connector, and a Luer part is inserted through the slit, so that the slit part deteriorates due to repeated opening and closing of the slit. When the Luer part is deteriorated, there is the risk that it will not be possible to sufficiently close the slit. In such a situation, the advantages of a closed connector cannot be satisfactorily demonstrated, and liquid in the channel space may leak to the outside. There is also the possibility that bacteria will grow at the periphery of the slit.

Embodiments of the present invention were devised in consideration of such a situation, with the objective of providing a connector that has a valve member that is reliably cut off from the outside when not in use, and wherein there is little risk of leakage or bacterial growth.

In order to accomplish the aforementioned objective, the features of the connector pertaining to the present invention are such that, in a connector provided with a housing having an opening open to the outside and a connection opening connected to a tube, and inside which a channel space is formed by means of which liquid can flow through the aforementioned connection opening, and having a valve member for supplying liquid from the outside into the aforementioned channel space that is attached to the aforementioned opening and can be opened and closed, said connector is provided with a main body that blocks the aforementioned opening in leakproof fashion and that can also be moved toward the aforementioned channel space by external pressure, and with a support part, connected to said main body and fastened to said housing, that acts on the aforementioned main body with elastic force when said main body is moved toward said channel space by external pressure. The main body also has an outside surface that faces the outside and an inside surface that faces said channel space when said opening is blocked in leakproof fashion. In addition, a connecting surface that connects to said channel space is formed in said outside surface when the main body is pushed into said channel space by external pressure.

With the connector of an embodiment of the present invention constituted as described above, the valve member attached to the opening of the housing is provided with a main body and a support part, and in addition, a connecting surface that connects to the channel space is formed in the outside surface of the main body when the main body is pushed into the channel space in the housing by external pressure. Therefore, the pushing member is pushed into the channel space along with the main body, and is connected to the channel space by the connecting surface being pushed from the outside by the pushing member, such as the Luer part of a syringe. If a liquid to be supplied is introduced through the pushing member at this stage, the liquid flows into the channel space from the connecting surface. The supply of liquid is accomplished in this way.

On the other hand, if the pushing member is removed from the connecting surface to eliminate the pushing force, the main body is returned to its original state (not pushed into the channel space) by the elastic force to which it is subjected by the support part. In the original state, the main body can block the opening in leakproof fashion, so the channel space is cut off from the outside by the main body. In this way, the valve member in the connector of embodiments of the present invention is a system wherein the outside surface itself of the main body is connected to the channel space by the main body being pushed into the channel space by a pushing force (pressure) from the outside, and this differs from a conventional system wherein the outside and the channel space are connected by a slit passing through the valve member. Thus, a conventional through slit formed in the valve member is not required. Since a through slit is not required, the valve member can be prevented from being semi-open when not in use (Luer part not inserted, no liquid supplied) as a result of deterioration of the through slit. It is therefore possible to realize a connector that is reliably cut off from the outside when not in use, and that has little risk of leakage or bacterial growth.

In the aforementioned embodiment of the present invention, the support part elastically supports the main body such that it is suspended from the opening when the main body is pushed toward the channel space by the pushing force (pressure) of a pushing member. When the pushing force (pressure) from the pushing member is released, the main body is returned to its original state by the elastic force generated by the support parts. The support part can be of any type, as long as it produces such an effect. For example, the support part can be constituted as a spring, and the spring could be fixed to the main body. The main body and the support part could also be molded integrally as a rubber member or the like. This would simplify the process of molding the valve member.

It is undesirable for a support part to be attached around the entire periphery of the main body without a gap. This is because when a support part is attached with no gap around the entire periphery of the main body, there will be no gap to join the outside surface and the channel space when the main body is pushed into the channel space. Therefore, there should be a gap, even a slight one, so that the outside surface connects to the channel space when the main body is pushed into the channel space. This gap can be in the form of a slit, or the support part can be attached to parts in the circumferential direction of the main body, with the regions unattached in the circumferential direction serving as the gap. Preferably, a form is conceivable in which multiple support arms are attached in positions that balance the main body (for example, symmetrical positions) and these multiple support arms are used as the support part to suspend the main body. If a valve opening and closing mechanism with such a suspension system is used, when the main body is pushed into the channel space, the channel space and the outside surface of the main body can be connected through the gap between the support arms.

The main body can also be of any form if it has an outside surface that faces the outside and an inside surface that faces the channel space, and it can block the opening in leakproof fashion. For example, it can have a disk shape like a milk bottle lid, and anything that achieves the aforementioned function can be used. However, because the opening must be blocked in leakproof fashion, it is preferable for the region contacting the opening to be larger, and a shape such as a round columnar rubber plug, the end surfaces of which serve as the outside surface and the inside surface, is satisfactory. If it has such a shape, its side peripheral surfaces can contact the opening over a wide area, and the fluid-tightness of the channel space can be sufficiently ensured.

The outside surface of the main body can also have any shape if it has a connecting surface that connects with the channel space by being displaced into the channel space by a pushing force (pressure) from the outside. For example, the outside surface can be formed in a flat plane, and the entire surface could connect with the channel space by being pushed into the channel space. In this case, the entire outside surface will be the connecting surface. A groove could also be formed in the planar outside surface, so that the aforementioned groove connects with the channel space when the outside surface is pushed into the channel space. In this case, the surface of the groove will be the connecting surface.

In another aspect, an inner slit is formed (a cut is formed) in the aforementioned main body that opens to the aforementioned inside surface and that extends in a direction from said inside surface to said outside surface.

When the outside surface of the main body is pushed by the Luer part of a syringe or the like, a pushing force or pressure acts in a direction from the outside toward the channel space, that is, a direction from the outside surface toward the inside surface. At the same time, when the main body is pushed toward the channel space by the pushing force, an elastic lifting force from the support part that elastically supports the main body acts to return the main body to its original position. The lifting force acts in a direction from the channel space toward the outside, that is, a direction from the inside surface toward the outside surface. Therefore, the main body is subjected to pushing force directed from the outside surface toward the inside surface, and to a lifting force in a direction opposite that of the pushing force. Therefore, a force couple caused by these forces acts on the main body.

When the action point on the inside surface of the main body part of the lifting force is positioned more toward the outer periphery than the pushing force action point on in the inside surface of the main body, the inside surface of the main body is subjected to a force whereby it is drawn from near the center (near the pushing force action point) to near the outer periphery (lifting force action point) by the force couple.

In this case, when an inner slit (a cut) that opens to the inside surface is formed and that also extends in a direction from the inside surface toward the outside surface, as in embodiments of the present invention, this inner slit opens due to the aforementioned force. A depression is formed in the outside surface of the main body in a position corresponding to the inner slit due to the opening of the inner slit. If the depressed part is caused to connect to the channel space, a liquid to be coinjected can be efficiently introduced into the channel space via the depressed portion.

In this way, the outside surface of the main body is not only pushed into the channel space and connected with the channel space, but the inside surface of the main body is opened using the force couple, a depression is formed in the outside surface, and the depression is connected to the channel space. Note that if the Luer part is pushed into the outside surface of the main body without producing such a depression, the opening at the tip of the Luer part will be pressed against the outside surface and it may not be possible for liquid medicine to be supplied from the Luer part. Concerning this point, a gap is produced between the opening at the tip of the Luer part and the outside surface by the formation of the aforementioned depression, so that liquid medicine can be supplied from this gap. In this way, embodiments of the present invention are useful for actual use.

Note that in aspects of the present invention as described above, the inside surface of the main body is subjected to a force in the direction from the center toward the outside by the force couple, and the action point at which lifting force from the support part acts on the inside surface should be positioned radially toward the outside from the pushing force action point. Thus, the place where the support part connects to the main body (that is, the position where the lifting force acts on the main body) should be positioned toward the outer periphery from the place where the pushing force acts on the main body (that is, the place where the main body is subjected to a pushing force by a Luer part or the like).

The lifting force from the support part should act on the main body from at least two different directions. This is so that the pulling force from the center to the outside in the inside surface is distributed in multiple directions, and the inside surface of the main body can be opened more reliably. For this reason, the support part should be connected with the main body in at least two points. More preferably, the support part should be connected to the main body in symmetrical regions centered on the part of the main body subjected to pushing force. In this case, since the pulling force acts nearly equally in the direction of the outer periphery, the inside surface of the main body can be opened evenly.

Note that it is preferable for an inner slit not to be formed in the inside surface of the main body on a line segment connecting the pushing force action point and action point of the lifting force from the support part, or in a direction parallel to that line segment. This is because the aforementioned direction is the direction in which a pulling force from the center toward the outside acts on the inside surface, and when the slit is formed in this direction, the slit cannot be opened. Thus, the inner slit should be formed in the inside surface in a direction other than the aforementioned direction. Most preferably, the inner slit should be formed in the inside surface of the main body in a direction perpendicular to a line joining the action point of the pushing force and the action point of the lifting force, that is, a direction perpendicular to a line joining the pushing where when the main body is pushed in by a pushing member and the lifting position where the support member acts on the main body.

It is also preferable that the inner slit be formed to divide the inside surface of the main body into two parts. When formed in this way, the inner slit is easily opened by the aforementioned pulling force from the center to the outside, and a depression formed in the outside surface of the main body, corresponding to opening of the inner slit, takes the form of a groove running along the inner slit. Thus, this groove-shaped depressed portion acts as a channel, and liquid medicine to be supplied can flow into the channel space along the groove-shaped depression. The liquid medicine to be supplied flows along the groove-shaped depression in this way, so that the liquid can be supplied effectively without the liquid medicine overflowing from the outside surface.

It is also preferable that an opening be made (a cut be formed) in the aforementioned outside surface and that an outer slit that extends in a direction from the aforementioned outside surface part toward the inside surface part be formed in the aforementioned main body. Due to the aforementioned force couple, a force causing folding toward the inside (toward the center) acts on the outside surface of the main body, but if an outer slit is formed, the outer slit is opened by the aforementioned force and the stress can be moderated. This improves the reliability of the valve member, and a longer service life can be achieved.

Note that it is preferable for the outer slit not to be formed on a line segment joining the pushing force action point and action point of the lifting force from the support in the outside surface of the main body, or in a direction parallel to that line segment. This is because the aforementioned direction is that in which the aforementioned force (force causing folding toward the inside) acts on the outside surface, and the slit cannot be opened if the slit is formed in this direction. Thus, the outer slit should be formed in a direction other than the aforementioned direction in the inside surface. Most preferably, the outer slit should be formed in a direction perpendicular to a line segment joining the action point of the pushing force and the action point of the lifting force in the inside surface of the main body, that is, a direction perpendicular to a line segment joining the pushing position where the main body is pushed in by a pushing member and the lifting position where the support member acts on the main body.

In this case, when an inner slit is formed, the planes in which the outer slit and inner slit are formed should be parallel. In addition, the outer slit should be furnished near the position where the support part is attached to the main body. The portion where the support part is attached to the main body is where a stress concentration most readily develops, so that concentration of stress can be moderated effectively by furnishing the outer slit near there.

The aforementioned housing is formed divided into a first portion that has the aforementioned opening and a second portion that has the aforementioned connection opening. The aforementioned connector should have an elastic means that is elastically connected to said first portion and said second portion so that the liquid in the aforementioned channel space does not leak outside through the gap between the dividing surface of said first portion and the dividing surface of said second portion. With the aforementioned constitution, when a Luer part or the like is pulled out from the opening, the first portion moves along with the Luer part due to frictional force acting between the valve member pressed against the opening and the Luer part, and the first portion and second portion separate. The elastic means is stretched by the first portion and the second portion separating, and the volume of the channel space formed inside the first portion and the second portion increases while fluid tightness is maintained. When the Luer part is pulled out farther, the elastic means stretches farther and the contraction force produced by the elastic means increases, and ultimately this contraction force exceeds the frictional force. In this case, the first portion separates from the Luer part to complete pulling out of the Luer part (Luer removal), the first portion moves toward the second portion due to the aforementioned contraction force, and the volume of the channel space decreases. The pressure in the channel space increases along with this decrease in volume of the channel space, and the channel space becomes positively pressurized. Here, when the channel space in the connector is negatively pressurized, there is the risk of undesirable backflow of the liquid in the medical tube connected to the connector, but with above-mentioned embodiments of the present invention, the interior of the channel space in the connector is positively pressurized when the Luer is removed, so backflow as described above can be prevented.

What is claimed is:

1. A connector comprising a housing having a plurality of connection ports, said housing defining a fluid flow through channel therein whereby said connection ports are selectably connectable via said through channel wherein one of said connection ports is an injection port, said injection port incorporating a valve member for sealingly closing said injection port whereby said valve member is arranged so as to be movable in a direction towards said through channel in response to an external pressure being applied thereto so as to open said injection port to fluid flow and wherein said housing comprises:

a first body part and a second body part, said second body part incorporating said injection port and wherein said first body part is connected to said second body part by an elastic member, said elastic member being arranged to exert a force on said second body part such that in an equilibrium state, said second body part is biased toward said through channel.

2. A connector according to claim 1 wherein said elastic member is arranged to exert a force on said second body part such that in an equilibrium state, said second body part is biased toward said first body part.

3. The connector according to claim 2 wherein said injection port is shaped so as to exert a frictional restraining force on a luer connector inserted into said injection port.

4. The connector according to claim 3 wherein said friction force is of a magnitude sufficient such that when said luer connector is withdrawn, said second body part is displaced away from said first body part.

5. The connector according to claim 1 wherein said elastic member is an elastic bellows.

6. A connector having a housing, said housing having an opening portion opened to the outside and a connecting port connected to a tube and which has a flow channel space that allows flow of liquid through said connecting port formed inside it, characterized in that the connector includes a closure comprising:

a valve member for attachment to said opening portion and for allowing a liquid from outside to flow into said flow channel space after opening of said valve member said valve member having a main body portion that seals said opening portion liquid tight and can be moved to the side of said flow channel space under a pressing force from the outside, and a supporting portion, which is connected to said main body portion and is engaged to said housing, and which has an elastic force that acts on said main body portion when said main body portion moves to the side of said flow channel space under the pressing force from the outside;

said main body portion has an outer surface facing the outside and the inner surface facing the flow channel space while said opening portion is blocked liquid tight;

and, on said outer surface, a connecting surface is formed that is connected to said flow channel space when said main body portion is pressed into the side of said flow channel space under the pressing force from outside and wherein said housing comprises:

a first body part and a second body part, said second body part incorporating said opening portion and wherein said first body part is connected to said second body part by an elastic member, said elastic member being arranged to exert a force on said second body part such that in an equilibrium state, said second body part is biased in a direction of the pressing force.

7. A connector according to claim 6 wherein said elastic member is arranged to exert a force on said second body part such that in an equilibrium state, said second body part is biased toward said first body part.

8. The connector according to claim 7 wherein said opening portion is shaped so as to exert a frictional restraining force on a luer connector when inserted into said opening portion.

9. The connector according to claim 8 wherein said friction force is of a magnitude sufficient such that when said luer connector is withdrawn, said second body part is displaced away from said first body part.

10. The connector according to claim 6 wherein said elastic member is an elastic bellows.

11. A connector having a housing, which has an opening portion opened to the outside and a connecting port connected to a tube and which has a flow channel space that allows flow of liquid through said connecting port formed inside it, characterized in that said connector comprises:

a valve member for attachment to said opening portion and for allowing a liquid from outside to flow into said flow channel space after opening of said valve member said valve member having a main body portion that seals said opening portion liquid tight and can be moved to the side of said flow channel space under the pressing force from the outside, and a supporting portion, which is connected to said main body portion and is engaged to said housing, and which has an elastic force that acts on said main body portion when said main body portion moves to the side of said flow channel space under the pressing force from the outside;

said main body portion has an outer surface facing the outside and the inner surface facing the flow channel space while said opening portion is blocked liquid tight;

and, on said outer surface, a connecting surface is formed that is connected to said flow channel space when said main body portion is pressed into the side of said flow channel space under the pressing force from outside and wherein said housing comprises:

a first body part and a second body part, said second body part incorporating said opening portion and wherein said first body part is connected to said second body part by an elastic member, said elastic member being arranged to exert a force on said second body cart such that in an equilibrium state, said second body part is biased in a direction of the pressing force.

12. A connector according to claim 11 wherein said elastic member is arranged to exert a force on said second body part such that in an equilibrium state, said second body part is biased toward said first body part.

13. The connector according to claim 12 wherein said opening portion is shaped so as to exert a frictional restraining force on a luer connector when inserted into said opening portion.

14. The connector according to claim 13 wherein said friction force is of a magnitude sufficient such that when said luer connector is withdrawn, said second body part is displaced away from said first body part.

15. The connector according to claim 11 wherein said elastic member is an elastic bellows.

16. A fluid through-flow connector having at least one connection port, said connection port comprising a connection port housing having an inner surface defining an inner volume and an outer surface, characterized in that said connector further comprises a sealing member, said sealing member having an inner portion extending within said inner volume and at least one outer portion extending externally of said housing, wherein said inner portion includes an inner slit extending from a lower surface of said inner portion and wherein said sealing member is of an elastically deformable material, wherein said sealing member is arranged such that it is deformable from a first closed state in which said sealing member is arranged in a fluid sealing configuration to a second open state in which said sealing member is arranged in a fluid non-sealing configuration and in which said inner portion is displaced into said inner volume and in which said at least one outer portion exerts a restoring force on said inner portion urging said inner portion to return to said first closed state, said deformation from said first closed state to said second open state being caused by the making of a connection to said connection port and wherein said housing comprises:
 a first body part and a second body part, said second body part incorporating said connection port and wherein said first body part is connected to said second body part by an elastic member, wherein said elastic member is arranged to exert a force on said second body part such that in an equilibrium state, said second body part is biased in a direction opposite the restoring force exerted on the inner portion.

17. A connector according to claim 16 wherein said elastic member is arranged to exert a force on said second body part such that in an equilibrium state, said second body part is biased toward said first body part.

18. The connector according to claim 17 wherein said connection port is shaped so as to exert a frictional restraining force on a luer connector when inserted into said connection port.

19. The connector according to claim 18 wherein said friction force is of a magnitude sufficient such that when said luer connector is withdrawn, said second body part is displaced away from said first body part.

20. The connector according to claim 16 wherein said elastic member is an elastic bellows.

* * * * *